United States Patent [19]

Woychik

[11] Patent Number: 5,789,651

[45] Date of Patent: Aug. 4, 1998

[54] ISOLATION AND CHARACTERIZATION OF AGOUTI: A DIABETES/OBESITY RELATED GENE

[75] Inventor: Richard P. Woychik, Knoxville, Tenn.

[73] Assignee: Martin Marietta Energy Systems, Inc., Oak Ridge, Tenn.

[21] Appl. No.: 465,293

[22] Filed: Jun. 5, 1995

Related U.S. Application Data

[62] Division of Ser. No. 64,385, May 21, 1993.

[51] Int. Cl.$^6$ .............................. C12N 5/00; C12N 15/00; C12N 15/09; C12N 15/63
[52] U.S. Cl. ..................... 800/2; 435/172.3; 435/69.1; 435/320.1; 435/91.2; 435/6.1; 536/23.1; 424/9.21
[58] Field of Search .................... 435/69.1, 172.1, 435/172.3, 320.1, 91.2, 6.1; 800/2; 536/23.1; 424/9.2, 9.21

[56] References Cited

U.S. PATENT DOCUMENTS 4,736,866  4/1988  Leder et al. .................... 800/1

FOREIGN PATENT DOCUMENTS 0 247 494  2/1987  European Pat. Off. ....... A01K 67/00

OTHER PUBLICATIONS

Wolff et al., Journal of Hereditary, vol. 77, pp. 151–158, 1986.
Rosenthal et al., Proc. Natl. Acad. Sci., USA, vol. 86, pp. 7780–7784, Oct. 1989.
Bultman et al., Proc. Natl. Acad. Sci., USA, vol. 88, p. 8062–8066, Sep. 1991.
Bultman et al., Cell, vol. 71, pp. 1195–1204, Dec. 24, 1992.
Balling et al., Cell, vol. 58, p. 337–347, Jul. 28, 1989.

*Primary Examiner*—Brian R. Stanton
*Assistant Examiner*—Jill D. Schmuck

[57] ABSTRACT

The present invention relates to the cloning and expression of the Agouti gene and analogous genes in transformed, transfected and transgenic mice. The present invention provides an animal model for the study of diabetes, obesity and tumors for the testing of potential therapeutic agents. The present invention provides oligonucleotide probes for the detection of the Agouti gene and mutations in the gene. The present invention also relates to the isolation and recombinant production of the Agouti gene product, production of antibodies to the Agouti gene product and their use as diagnostic and therapeutic agents.

6 Claims, 9 Drawing Sheets

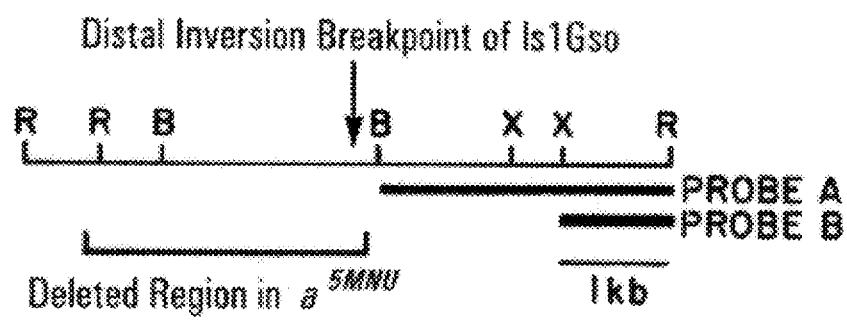
FIG. 1A
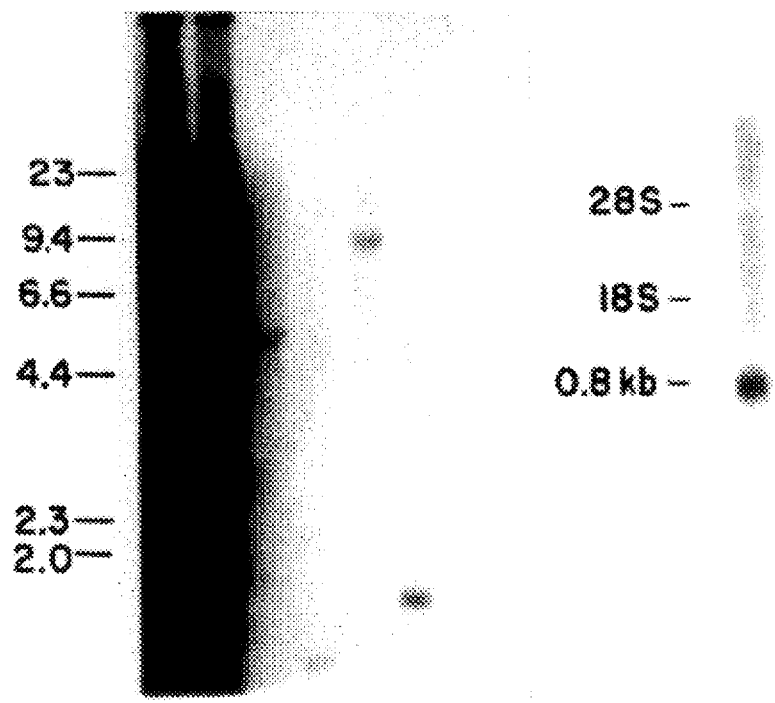
FIG. 1B
FIG. 1C

FIG. 2

```
TTCAAGGACAGGAAAGACATTCTGGCCTGGCTTCCCTTAGGGGAGCTGATGCGGAATAGAGTC        63  SEQ ID No.:1
                  ↓
ACTTGTGCTGCTTCTCAGG ATG GAT GTC ACC CGC CTA CTC CTG GCC ACC CTA       115
SEQ ID No.: II      Met Asp Val Thr Arg Leu Leu Leu Ala Thr Leu        11

GTG AGC TTC CTG TGC TTC TTC ACC GTC CAC AGC CAC CTG GCA CTC GAG       163
Val Ser Phe Leu Cys Phe Phe Thr Val His Ser His Leu Ala Leu Glu        27
                    •

PO₄                     PO₄           ★
GAG ACG CTT GGA GAT GAC AGG AGT CTG CGG AGT AAC TCC TCC ATG AAC       211
Glu Thr Leu Gly Asp Asp Arg Ser Leu Arg Ser Asn Ser Ser Met Asn        43

↓                    PO₄
TCG CTG GAT TTC TCC TCT GTT TCT ATC GTG GCA CTG AAC AAG AAA TCC       259
Ser Leu Asp Phe Ser Ser Val Ser Ile Val Ala Leu Asn Lys Lys Ser        59

PO₄                                          PO₄ PO₄  ↓
AAG AAG ATC AGC AGA AAA GAA GCC GAG AAG CGG AAG AGG TCT TCC AAG       307
Lys Lys Ile Ser Arg Lys Glu Ala Glu Lys Arg Lys Arg Ser Ser Lys        75

PO₄
AAA AAG GCT TCG ATG AAG AAG GTG GCA AGG CCC CCG CCA CCT TCG CCC       355
Lys Lys Ala Ser Met Lys Lys Val Ala Arg Pro Pro Pro Pro Ser Pro        91

PO₄
TGC GTG GCC ACC CGC GAC AGC TGC AAG CCA CCC GCA CCC GCC TGC TGC       403
Cys Val Ala Thr Arg Asp Ser Cys Lys Pro Pro Ala Pro Ala Cys Cys       107
                              •                         •   •

PO₄
GAC CCG TGC GCC TCC TGC CAG TGC CGT TTC TTC GGC AGC GCC TGC ACC       451
Asp Pro Cys Ala Ser Cys Gln Cys Arg Phe Phe Gly Ser Ala Sys Thr       123
        •       •       •   •                           •

TGT CGA GTA CTC AAC CCC AAC TGC TGA CGCAGCTTCTTCGCTGCGCGCGCAGCT       505
Cys Arg Val Leu Asn Pro Asn Cys End                                   131
    •                       •

TCGGGAACGGGTGATTGGGCGGGGCTTCAGGGTCCCGCGCTTCTAGGCTGAGGGGCGGGTCTC       568

TGTGGGTGGGGCTTGTGGGTGGGCGTGGTCAGTGGTTGTGACTTGTGGGCGCTTTCAAAAAAC       631

CGGTTTTCTAGGAAACCTAGTGGAAGCTAAAATCAGAATACAATAATATTTTTAGGCTGCC ( A )  692
```

FIG. 3A

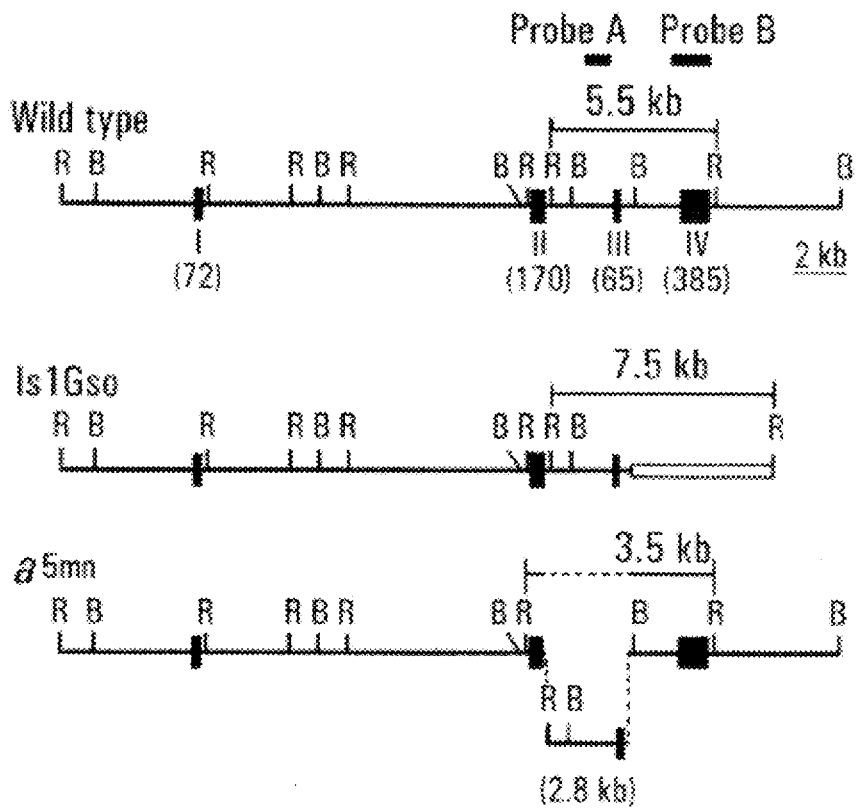

FIG. 3B

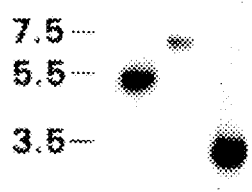

FIG. 3C

| | | |
|---|---|---|
| Wild type | CATTGAGGACAACGTCC CTAGGCTGTGGGAGTGTGTCTGTATGTAGCGTTT | SEQ ID No.:2 |
| Is1Gso | CATTGAGGACAACGTCC gcggagtaaatcgaacccggctacacttttatgt | SEQ ID No.:3 |

| | | |
|---|---|---|
| Wild type | AAGTCAAGATGCTTGGTGGACTTGGTTTTCTTTAGCGTTAATG ACATTTTAA | SEQ ID NO.:4 |
| 5'$\partial^{SMNU}$ | AAGTCAAGATGCTTGGTGGACTTGGTTTTCTTTAGCGTTAATG ---------- | SEQ ID No.:5 |

| | | |
|---|---|---|
| Wild type | AGGAGGCTGAGGC ACGTAGATCTGAGTTTGAGGCCAGCCTGGTCTACAGAGT | SEQ ID. No.:6 |
| 3'$\partial^{SMNU}$ | ---------- ACGTAGATCTGAGTTTGAGGCCAGCCTGGTCTACAGAGT | SEQ ID. No.:7 |

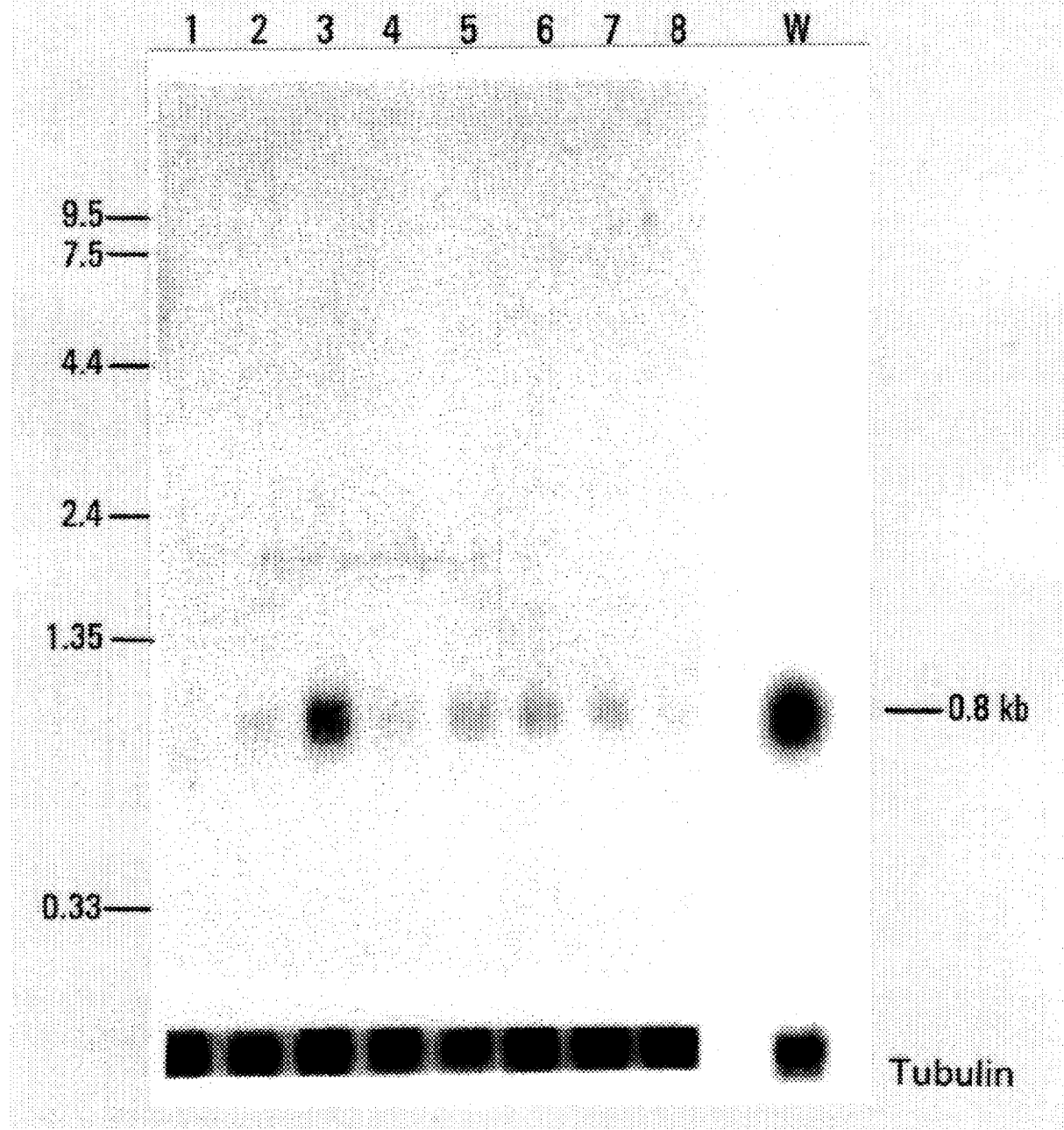

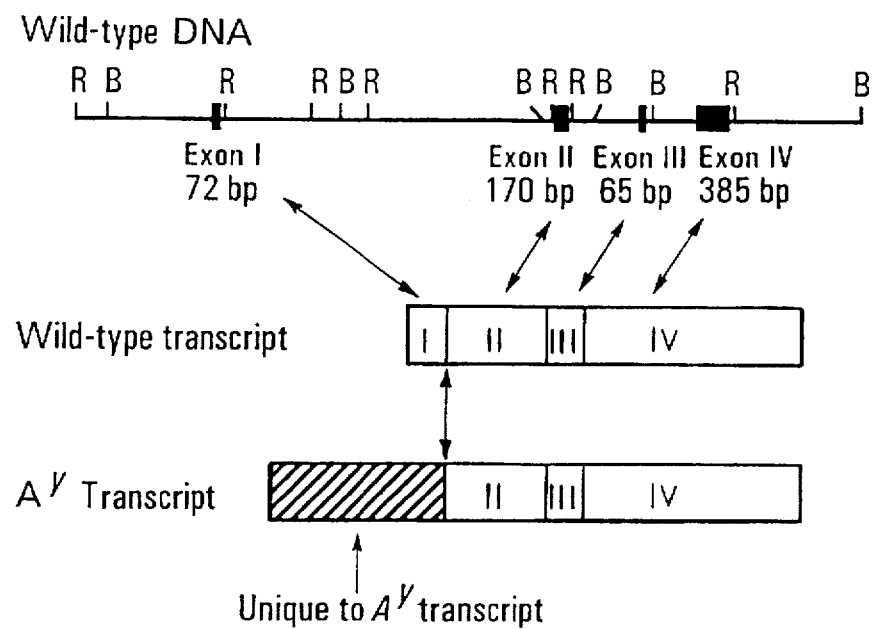

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
    ( A ) LENGTH: 692 nucleotides
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Mouse
    ( B ) STRAIN: C3H Strain
    ( D ) DEVELOPMENTAL STAGE: Neonatal or Adult
    ( F ) TISSUE TYPE: Neonatal skin or adult Ay Is1Gso kidney or testis.

( v i i ) IMMEDIATE SOURCE:
    ( A ) LIBRARY: Neonatal skin cDNA ( v i i i ) POSITION IN GENOME:
    ( A ) CHROMOSOME/SEGMENT: Agouti locus of mouse chromosome 2.

( i x ) FEATURE:
    ( A ) NAME/KEY: Agouti locus
    ( C ) IDENTIFICATION METHOD: Experimental
    ( D ) OTHER INFORMATION: In addition to hair color in mice, the Agouti gene is responsible for embryonic lethality, obesity, diabetes, and the development of tumor in a wide variety of tissues.

( x ) PUBLICATION INFORMATION:
    ( A ) AUTHORS: Scott J. Boltman, Edward J. Michaud, and Richard P. Woychik
    ( B ) TITLE: Molecular Characterization of the Mouse Agouti Locus
    ( C ) JOURNAL: Submitted to CELL
    ( K ) RELEVANT RESIDUES IN SEQ ID NO: 1: FROM 1 TO 692

( x i ) SEQUENCE DESCRIPTION: SEQ ID NO: 1:

```
TTCAAGGACA  GGAAAGACAT  TCTGGCCTGG  CTTCCCTTAG  GGGAGCTGAT  GCGGAATAGA                    60

GTCACTTGTG  CTGCTTCTCA  GG ATG GAT GTC ACC CGC CTA CTC CTG GCC ACC                       112
               Met Asp Val Thr Arg Leu Leu Leu Ala Thr
               1               5                   10

CTA GTG AGC TTC CTG TGC TTC TTC ACC GTC CAC AGC CAC CTG GCA CTC                          160
Leu Val Ser Phe Leu Cys Phe Phe Thr Val His Ser His Leu Ala Leu
             15                  20                  25

GAG GAG ACG CTT GGA GAT GAC AGG AGT CTG CGG AGT AAC TCC TCC ATG                          208
Glu Glu Thr Leu Gly Asp Asp Arg Ser Leu Arg Ser Asn Ser Ser Met
             30                  35                  40

AAC TCG CTG GAT TTC TCC TCT GTT TCT ATC GTG GCA CTG AAC AAG AAA                          256
Asn Ser Leu Asp Phe Ser Ser Val Ser Ile Val Ala Leu Asn Lys Lys
         45                  50                  55

TCC AAG AAG ATC AGC AGA AAA GAA GCC GAG AAG CGG AAG AGG TCT TCC                          304
Ser Lys Lys Ile Ser Arg Lys Glu Ala Glu Lys Arg Lys Arg Ser Ser
```

-continued

```
                60                          65                          70
AAG  AAA  AAG  GCT  TCG  ATG  AAG  AAG  GTG  GCA  AGG  CCC  CCG  CCA  CCT  TCG       352
Lys  Lys  Lys  Ala  Ser  Met  Lys  Lys  Val  Ala  Arg  Pro  Pro  Pro  Pro  Ser
75                       80                      85                      90

CCC  TGC  GTG  GCC  ACC  CGC  GAC  AGC  TGC  AAG  CCA  CCC  GCA  CCC  GCC  TGC       400
Pro  Cys  Val  Ala  Thr  Arg  Asp  Ser  Cys  Lys  Pro  Pro  Ala  Pro  Ala  Cys
                    95                      100                     105

TGC  GAC  CCG  TGC  GCC  TCC  TGC  CAG  TGC  CGT  TTC  TTC  GGC  AGC  GCC  TGC       448
Cys  Asp  Pro  Cys  Ala  Ser  Cys  Gln  Cys  Arg  Phe  Phe  Gly  Ser  Ala  Cys
               110                      115                     120

ACC  TGT  CGA  GTA  CTC  AAC  CCC  AAC  TGC  TGACGCAGCT  TCTTCGCTGC                  495
Thr  Cys  Arg  Val  Leu  Asn  Pro  Asn  Cys
          125                      130

GCGCGCAGCT  TCGGGAACGG  GTGATTGGGC  GGGGCTTCAG  GGTCCCGCGC  TTCTAGGCTG               555

AGGGGCGGGT  CTCTGTGGGT  GGGGCTTGTG  GGTGGGCGTG  GTCAGTGGTT  GTGACTTGTG               615

GGCGCTTTCA  AAAAACCGGT  TTTCTAGGAA  ACCTAGTGGA  AGCTAAAATC  AGAATACAAT               675

AATATTTTTA  GGCTGCM                                                                  692
```

( 2 ) INFORMATION FOR SEQ ID NO: 2:

( i ) SEQUENCE CHARACTERISTICS:
        ( A ) LENGTH: 51 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Mouse
        ( B ) STRAIN: Wild ( v i i ) IMMEDIATE SOURCE:
        ( A ) LIBRARY: genomic ( v i i i ) POSITION IN GENOME:
        ( A ) CHROMOSOME/SEGMENT: Agouti locus of mouse chromosome 2
           comparable to SEQ ID NO: 3.

( i x ) FEATURE:
        ( A ) NAME/KEY: Agouti locus
        ( C ) IDENTIFICATION METHOD: Experimental
        ( D ) OTHER INFORMATION: In addition to hair color in mice, the
           Agouti gene is responsible for embryonic lethality,
           obesity, diabetes, and the development of tumor in a
           wide variety of tissues.

( x ) PUBLICATION INFORMATION:
        ( A ) AUTHORS: Scott J. Boltman, Edward J. Michaud, and Richard
           P. Woychik
        ( B ) TITLE: Molecular Characterization of the Mouse Agouti
           Locus
        ( C ) JOURNAL: Submitted to CELL
        ( K ) RELEVANT RESIDUES IN SEQ ID NO: 2: FROM 1 TO 51

( x i ) SEQUENCE DESCRIPTION: SEQ ID NO: 2:

```
CATTGAGGAC  AACGTCCCTA  GGCTGTGGGA  GTGTGTCTGT  ATGTAGCGTT  T                        51
```

( 2 ) INFORMATION FOR SEQ ID NO: 3:

( i ) SEQUENCE CHARACTERISTICS:
        ( A ) LENGTH: 51 nucleotides
        ( B ) TYPE: nucleic acid
        ( C ) STRANDEDNESS: single
        ( D ) TOPOLOGY: linear (i i) MOLECULE TYPE: genomic DNA (i i i) HYPOTHETICAL: NO (i v) ANTI-SENSE: NO (v i) ORIGINAL SOURCE:
    (A) ORGANISM: Mouse
    (B) STRAIN: Homozygous for IS1Gso mutation (v i i) IMMEDIATE SOURCE:
    (A) LIBRARY: genomic (v i i i) POSITION IN GENOME:
    (A) CHROMOSOME/SEGMENT: Distal inversion breakpoint of Is1Gso
    mutation in Agouti locus of mouse chromosome 2.

(i x) FEATURE:
    (A) NAME/KEY: Agouti locus
    (C) IDENTIFICATION METHOD: Experimental
    (D) OTHER INFORMATION: In addition to hair color in mice, the
    Agouti gene is responsible for embryonic lethality,
    obesity, diabetes, and the development of tumor in a wide
    variety of tissues.

(x) PUBLICATION INFORMATION:
    (A) AUTHORS: Scott J. Boltman, Edward J. Michaud, and Richard
    P. Woychik
    (B) TITLE: Molecular Characterization of the Mouse Agouti
    Locus
    (C) JOURNAL: Submitted to CELL
    (K) RELEVANT RESIDUES IN SEQ ID NO: 3: FROM 1 TO 51

(x i) SEQUENCE DESCRIPTION: SEQ ID NO: 3:

```
CATTGAGGAC AACGTCCGCG GAGTAAATCG AACCCGGCTA CACTTTTATG T                 51
```

(2) INFORMATION FOR SEQ ID NO: 4:

(i) SEQUENCE CHARACTERISTICS:
        (A) LENGTH: 52 nucleotides
        (B) TYPE: nucleic acid
        (C) STRANDEDNESS: single
        (D) TOPOLOGY: linear (i i) MOLECULE TYPE: genomic DNA (i i i) HYPOTHETICAL: NO (i v) ANTI-SENSE: NO (v i) ORIGINAL SOURCE:
        (A) ORGANISM: Mouse
        (B) STRAIN: Wild (v i i) IMMEDIATE SOURCE:
        (A) LIBRARY: genomic (v i i i) POSITION IN GENOME:
        (A) CHROMOSOME/SEGMENT: Agouti locus of mouse chromosome 2
        comparable to SEQ ID NO: 5.

(i x) FEATURE:
        (A) NAME/KEY: Agouti locus
        (C) IDENTIFICATION METHOD: Experimental
        (D) OTHER INFORMATION: In addition to hair color in mice, the
        Agouti gene is responsible for embryonic lethality,
        obesity, diabetes, and the development of tumor in a wide
        variety of tissues.

(x) PUBLICATION INFORMATION:
        (A) AUTHORS: Scott J. Boltman, Edward J. Michaud, and Richard
        P. Woychik
        (B) TITLE: Molecular Characterization of the Mouse Agouti
        Locus
        (C) JOURNAL: Submitted to CELL
        (K) RELEVANT RESIDUES IN SEQ ID NO: 4: FROM 1 TO 52

( x i ) SEQUENCE DESCRIPTION: SEQ ID NO: 4:

AAGTCAAGAT GCTTGGTGGA CTTGGTTTTC TTTAGCGTTA ATGACATTTT AA  52

( 2 ) INFORMATION FOR SEQ ID NO: 5:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Mouse
        ( B ) STRAIN: Homozygous for a5MNU ( v i i ) IMMEDIATE SOURCE:
        ( A ) LIBRARY: genomic ( v i i i ) POSITION IN GENOME:
        ( A ) CHROMOSOME/SEGMENT: 5'deletion breakpoint of a5MNU
            mutation in Agouti locus of mouse chromosome 2.

( i x ) FEATURE:
        ( A ) NAME/KEY: Agouti locus
        ( C ) IDENTIFICATION METHOD: Experimental
        ( D ) OTHER INFORMATION: In addition to hair color in mice, the
            Agouti gene is responsible for embryonic lethality,
            obesity, diabetes, and the development of tumor in a
            wide variety of tissues.

( x ) PUBLICATION INFORMATION:
        ( A ) AUTHORS: Scott J. Boltman, Edward J. Michaud, and Richard
            P. Woychik
        ( B ) TITLE: Molecular Characterization of the Mouse Agouti
            Locus
        ( C ) JOURNAL: Submitted to CELL
        ( K ) RELEVANT RESIDUES IN SEQ ID NO: 1: FROM 1 TO 43

( x i ) SEQUENCE DESCRIPTION: SEQ ID NO: 5:

AAGTCAAGAT GCTTGGTGGA CTTGGTTTTC TTTAGCGTTA ATG  43

( 2 ) INFORMATION FOR SEQ ID NO: 6:

( i ) SEQUENCE CHARACTERISTICS:
        ( A ) LENGTH: 52 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Mouse
        ( B ) STRAIN: Wild ( v i i ) IMMEDIATE SOURCE:
        ( A ) LIBRARY: genomic ( v i i i ) POSITION IN GENOME:
        ( A ) CHROMOSOME/SEGMENT: Agouti locus of mouse chromosome 2
            comparable to SEQ ID NO. 7.

( i x ) FEATURE:
        ( A ) NAME/KEY: Agouti locus
        ( C ) IDENTIFICATION METHOD: Experimental
        ( D ) OTHER INFORMATION: In addition to hair color in mice, the -continued Agouti gene is responsible for embryonic lethality,
obesity, diabetes, and the development of tumor in a wide
variety of tissues.

( x ) PUBLICATION INFORMATION:
( A ) AUTHORS: Scott J. Boltman, Edward J. Michaud, and Richard
P. Woychik
( B ) TITLE: Molecular Characterization of the Mouse Agouti
Locus
( C ) JOURNAL: Submitted to CELL
( K ) RELEVANT RESIDUES IN SEQ ID NO: 6: FROM 1 TO 52

( x i ) SEQUENCE DESCRIPTION: SEQ ID NO: 6:

AGGAGGCTGA GGCACGTAGA TCTGAGTTTG AGGCCAGCCT GGTCTACAGA GT        52

( 2 ) INFORMATION FOR SEQ ID NO: 7:

( i ) SEQUENCE CHARACTERISTICS:
( A ) LENGTH: 39 nucleotides
( B ) TYPE: nucleic acid
( C ) STRANDEDNESS: single
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
( A ) ORGANISM: Mouse
( B ) STRAIN: Homozygous for a5MNU ( v i i ) IMMEDIATE SOURCE:
( A ) LIBRARY: genomic ( v i i i ) POSITION IN GENOME:
( A ) CHROMOSOME/SEGMENT: 3'deletion breakpoint of a5MNU
mutation in Agouti locus of mouse chromosome 2.

( i x ) FEATURE:
( A ) NAME/KEY: Agouti locus
( C ) IDENTIFICATION METHOD: Experimental
( D ) OTHER INFORMATION: In addition to hair color in mice, the
Agouti gene is responsible for embryonic lethality,
obesity, diabetes, and the development of tumor in a wide
variety of tissues.

( x ) PUBLICATION INFORMATION:
( A ) AUTHORS: Scott J. Boltman, Edward J. Michaud, and Richard
P. Woychik
( B ) TITLE: Molecular Characterization of the Mouse Agouti
Locus
( C ) JOURNAL: Submitted to CELL
( K ) RELEVANT RESIDUES IN SEQ ID NO: 7: FROM 1 TO 43

( x i ) SEQUENCE DESCRIPTION: SEQ ID NO: 7:

ACGTAGATCT GAGTTTGAGG CCAGCCTGGT CTACAGAGT        39

( 2 ) INFORMATION FOR SEQ ID NO: 8:

( i ) SEQUENCE CHARACTERISTICS:
( A ) LENGTH: 13 nucleotides
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Mouse
( B ) STRAIN: Wild -continued ( F ) TISSUE TYPE: Adult kidney and testis ( v i i ) IMMEDIATE SOURCE:
        ( B ) CLONE: Wild-type cDNA clones ( v i i i ) POSITION IN GENOME:
        ( A ) CHROMOSOME/SEGMENT: transition point of exon 1 from exon
            2 in Agouti locus of mouse chromosome 2.

( i x ) FEATURE:
        ( A ) NAME/KEY: Agouti locus
        ( C ) IDENTIFICATION METHOD: Experimental
        ( D ) OTHER INFORMATION: In addition to hair color in mice, the
            Agouti gene is responsible for embryonic lethality,
            obesity, diabetes, and the development of tumor in a wide
            variety of tissues.

( x i ) SEQUENCE DESCRIPTION: SEQ ID NO: 8:

TTGTGCTGCT TCT                                                     13

( 2 ) INFORMATION FOR SEQ ID NO: 9:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mouse
        ( B ) STRAIN: Heterozygote for Lethal yellow (Ay)
        ( F ) TISSUE TYPE: Adult kidney and testis ( v i i ) IMMEDIATE SOURCE:
        ( A ) LIBRARY: Adult kidney and testis cDNA clones ( v i i i ) POSITION IN GENOME:
        ( A ) CHROMOSOME/SEGMENT: transition point of exon 1 from exon
            2 in Agouti locus of mouse chromosome 2.

( i x ) FEATURE:
        ( A ) NAME/KEY: Agouti locus
        ( C ) IDENTIFICATION METHOD: Experimental
        ( D ) OTHER INFORMATION: In addition to hair color in mice, the
            Agouti gene is responsible for embryonic lethality,
            obesity, diabetes, and the development of tumor in a wide
            variety of tissues.

( x i ) SEQUENCE DESCRIPTION: SEQ ID NO: 9:

GGCGCGGGCT TCT                                                     13

( 2 ) INFORMATION FOR SEQ ID NO: 10:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( i i ) MOLECULE TYPE: Genomic ( i i i ) HYPOTHETICAL: NO ( i v ) ANTI-SENSE: NO ( v i ) ORIGINAL SOURCE:
        ( A ) ORGANISM: Mouse
        ( B ) STRAIN: Heterozygote for Lethal yellow (Ay)

( v i i ) IMMEDIATE SOURCE:

```
            ( A ) LIBRARY: Genomic ( v i i i ) POSITION IN GENOME:
            ( A ) CHROMOSOME/SEGMENT: corresponding genomic region of the
                5' end of the Ay cDNA set forth in SEQ ID NO: 9.

( i x ) FEATURE:
            ( A ) NAME/KEY: Agouti locus
            ( C ) IDENTIFICATION METHOD: Experimental
            ( D ) OTHER INFORMATION: In addition to hair color in mice, the
                Agouti gene is responsible for embryonic lethality,
                obesity, diabetes, and the development of tumor in a wide
                variety of tissues.

( x i ) SEQUENCE DESCRIPTION: SEQ ID NO: 10:

GGCGCGGGTG AGT                                                              1 3
```

ISOLATION AND CHARACTERIZATION OF AGOUTI: A DIABETES/OBESITY RELATED GENE

This is a divisional of co-pending application Ser. No. 08/064,385 filed May 21, 1993.

FIELD OF INVENTION

This invention relates to the isolation of a gene in which expression of the gene product correlates with the development of insulin independent diabetes, hyperamylinemia, neoplasms and obesity in animals. Another aspect of the invention is the use of the gene in transgenic animals as an animal model for such diseases as insulin independent diabetes, obesity, hyperamylinemia, and neoplasms. The invention also relates to the gene product, antibodies to the gene product and their use as diagnostics and therapeutics.

BACKGROUND OF THE INVENTION

The agouti locus (a) in chromosome 2 regulates the differential production of black and yellow pigment granules that give rise the agouti coat color of the mouse. Agouti coloration, which is the true wild-type coat color of mice, is unusual in that it arises not from a homogenous pigmentation of the pelage, but rather from a banded coloration pattern in which each hair is black with a subapical band of yellow. One of the most interesting aspects of the agouti locus is that it functions within the microenvironment of the hair follicle (Silver, W. K. and Russell, 1955, *J. Exp. Zool.*, 130:199–220; Silvers, W. K. 1958, *J. Exp. Zool.* 137:181–188; Silvers, W. K. 1958, *J. Exp. Zool.* 137:189–198; Silvers, W. K. 1961 *Science* 134:368–373; Silvers, W. K. 1979 in: *The Coat Colors of Mice: A Model for Mammalian Gene Action and Interaction*, New York, N.Y., Springer-Verlag, pp. 6–44), unlike may other coat color genes, which act in a cell-autonomous manner within the melanocytes. Therefore, agouti must be regulating coat pigmentation by some direct or indirect form of intercellular signaling within the follicular environment.

Like many other genes that play a role in the regulation of coat pigmentation in the mouse, the agouti locus contributes to essential developmental processes unrelated to pigmentation (Geissler, E. N. et al., 1988, *Cell* 55:185–192; Witte, O. N. 1990 *Cell* 63:5–6; Epstein, D. J. et al. 1991 *Cell* 67:767–774; Mercer, J. A. et al. 1991 *Nature* 349:709–713). For example, some of the individual alleles at the agouti locus are associated with embryonic lethality, obesity, diabetes, and the development of tumors in a wide variety of tissues. In fact, the lethal yellow ($A^y$) mutation at agouti was the first embryonic lethal mutation to be characterized in the mouse (Cuènot, L. 1905 *Arch. Zool. Exp. Gen.* 3:123–132). Embryos homozygous for $A^y$ die very early in development, around the time of implantation, possibly owing to a defect in trophectoderm differentiation (Eaton, G. J. and Green, M. M. 1963 *Genetica* 34:155–161; Calarco, P. G. and Pederson, R. A. 1976; Papaioannou, V. E. and Gardner, R. L. 1979 *J. Embryol. Exp. Morphol.* 52: 153–163).

Genetic analyses of numerous a locus mutants have been ongoing for nearly a century, and have led to the identification of at least 18 dominant and recessive alleles and pseudoalleles of agouti (Silvers, W. K. 1979 ibid; Green, M. C. 1989. In: Genetic Variants and Strains of the Laboratory Mouse, M. F. Lyon and A. G. Searle, eds., Oxford, Oxford University Press, pp. 17–20). Different combinations of alleles account for an array of different phenotypes, ranging from subtle differences in coat color as compared with the wild type, to drastic changes in the distribution of pigmentation in different regions of the animal, particularly across the dorso-ventral surface. An intricate dominance hierarchy exists in which alleles associated with phaeomelanin (yellow) production are generally dominant over alleles associated with eumelanin (Black or brown, depending on alleles at other loci) production. This relationship is exemplified by several alleles that date back to the mouse fancy: lethal yellow ($A_y$), which confers an all-yellow phenotype in the heterozygous condition, black-and-tan($a^t$), which gives rise to an all-black dorsum and an all-yellow ventrum (Dunn, L. C. 1928 *Proc. Natl. Acad. Sci. USA* 14:816–819), nonagouti (a), which gives rise to a predominantly black phenotype, except for small amounts of phaeomelanin around the pinnae, nipples, and perineum, and extreme nonagouti ($a^e$), which confers a completely black phenotype (Hollander, W. F. and Gowen, J. W. 1956 *J. Hered.* 47:221–224).

The large number of alleles and the wide range of phenotypes associated with the agouti locus have been used as evidence by some investigators to propose that the agouti locus is comprised of multiple "mini-loci" and not a single gene. According to this hypothesis, each gene of the mini-locus plays a role in regulating pigmentation in different parts of the body, particularly over the dorsal and ventral surfaces, and around the pinae, nipples, and perineum. Support for this assertion stems from the finding that changes from yellow to black pigmentation proceed from the dorsal to the ventral regions as one progresses from the most dominant to the most recessive mutation of the agouti allelic series. For example, phaeomelanin progressively disappears from the mid-dorsum with $A^i$/a ($A^i$, intermediate yellow), from the lateral dorsum with $a^t/a^t$, from the ventral surface with a/a, and from the pinnae, nipples, and perineum with $a^e$. With the mini-locus hypothesis, different genes should be affected by mutations associated with the individual alleles in the hierarchy. The present invention demonstrates that the structure and expression of the same gene is affected by mutations at the top ($A^y$), middle ($a^t$ and a), and bottom ($a^e$) of the allelic series. These results disprove the mini-locus hypothesis.

Although the agouti alleles have been extensively characterized with classical genetic techniques, the structure of the gene(s) responsible for a locus function had not been determined until the present invention. Attempts by others to isolate the gene using positional cloning techniques, failed to isolate the gene (Barsh and Epstein 1989a. *Genomics* 121:811–818; Siracusa et al. 1987 a *Genetics* 117:93–100; Siracusa et al. 1989 *Genetics* 122:669–679; Siracusa 1991. *Ann. N.Y. Acad. Sci* 642:419–430.).

A radiation-induced inversion mutation, called Is(17;In2) Id,aJGso (abbreviated Is1Gso), which contains DNA breakpoints in the limb deformity (ld) and agouti loci, two regions that are normally separated by 22 cM on chromosome 2 (Woychik, R. P. et al. 1990a *Proc. Natl. Acad. Sci., USA* 87:2588–2592; Bultman, S. J. et al. 1991 *Proc. Natl. Acad. Sci., USA* 88:8062–8066) was previously described. Utilizing a DNA probe from the $ld^{Hd}$ insertional mutant (Woychik, R. P. et al. 1985 *Nature* 318:36–40), 22 cM were jumped with the inversion which allowed a region of DNA that maps to the agouti locus to be identified (Woychik et al. 1990a, ibid). Moreover, this region also hybridizes to sequences that are rearranged in several agent-induced a locus mutations (Bultman, S. J. et al. 1991, ibid). Here we present the molecular characterization of a gene from this region of DNA that is structurally altered in several a locus mutations and is expressed in a manner appropriate for agouti function. The present invention demonstrates that there is one gene associated with the a locus.

SUMMARY OF THE INVENTION

The present invention relates to nucleic acid sequences in which expression of the gene product is associated with the development of diabetes, obesity, hyperamylinemia and the development of tumors in a wide variety of tissues in animals. Such nucleic acid sequences may be synthetic DNA or RNA sequences or isolated natural DNA or RNA sequences and any functionally equivalent nucleic acid sequences, analogs and portions thereof. Such DNA sequences may be complementary DNA (cDNA) or genomic DNA. The present invention also relates to anti-sense nucleic acid sequences.

It is also an object of this invention to provide transgenic animals capable of promoting a disease such as obesity, diabetes hyperamylinemia and neoplasms in the transfected animals with expression of the gene product.

In general, the invention features a transgenic non-human vertebrate animal (preferably a mammal, e.g., a cow, pig, mouse, rabbit, rat and the like) containing germ cells and somatic cells which contain a gene which is substantially homologous with a vertebrate gene or a portion thereof which is capable of promoting (i.e., increases the probability of developing) the diseases: non-insulin-dependent diabetes, obesity, neoplasms and hyperamylinemia. The gene (i.e., the gene as it exists prior to introduction into the animal) is introduced into the animal, or an ancestor of the animal, at an embryonic stage (preferably the one-cell, or fertilized oocyte, stage, and generally not later than about the 8-cell stage). The gene preferably is substantially homologous with (i.e., greater than 50% homologous in terms of encoded amino acid sequence) a naturally occurring vertebrate gene or portion thereof or their vertebrate counterparts, preferably the murine Agouti gene or the human Agouti gene counterpart. In addition, the gene may be a vertebrate-derived gene or sequence thereof, and also substantially homologous genes found from other sources such as invertebrates, plants, virus, protozoas, bacteria and the like which function in an equivalent manner in the transfected animal.

DNA sequences of the genes of Agouti are shown in FIGS. 2 and 9. Any genomic, recombinant gene or functionally equivalent sequence thereof derived from this sequence or a substantially homologous sequence or portions thereof may be used to produce the transgenic animals of the invention.

There are several means by which transgenic animals can be made. One method involves the use of a transfecting retrovirus containing the transgene. Another method involves directly injecting the transgene into the embryo. Yet another method employs the embryonic stem cell methodology known to workers in this field.

Preferably, transcription of the gene is under the control of a promoter sequence different from the promoter sequence controlling transcription of the endogenous coding sequence. Transcription of the gene can also be under the control of a synthetic promoter sequence. The promoter sequence controlling transcription of the gene may be active (i.e., can promote gene expression) in all tissues for example Beta-actin promoter or may be a tissue specific promoter such as the insulin promoter, which would direct expression to the β-cells within the pancreas. The promoter that controls transcription of the recombinant gene may be of viral origin; example are promoters sometimes derived from mouse mammary tumor virus (MMTV) and cytomegalovirus (CMV).

Introduction of the gene at the fertilized oocyte stage ensures that the gene sequence will be present in the germ cells and somatic cells of the transgenic "founder" animal. (As used herein, founder (abbreviated "F") means the animal into which the gene was originally introduced at the one cell mouse embryo stage.) The presence of the gene sequence in the germ cells of the transgenic founder animal in turn means that some of the founder animal's descendants will carry the gene sequence in germ cells and somatic cells. Introduction of the gene sequence at a later embryonic stage might result in the gene's absence from some somatic cells or germ cells of the founder animal, but the descendants of such an animal that inherit the gene will carry the gene in all of their germ cells and somatic cells.

The transgenic animals of the invention can be used as models to test for agents potentially useful in the treatment of non-insulin-dependent diabetes, obesity, hyperamylinemia and neoplasms. The agent to be tested can be administered to an animal of the invention and the disease state monitored. The transgenic animals of the invention can also be used to test a material suspected of promoting non-insulin-dependent diabetes, obesity, hyperamylinemia and neoplasms. The transgenic animals of the present invention are useful for screening potentially diagnostic reagents for the diagnosis or prognosis of diabetes, obesity and cancer in humans or diagnostic reagents which may be predictive of the development of such diseases.

Such therapeutic and diagnostic reagents may be peptides, antibodies, cytokines, growth factors, growth inhibitors, chemicals, chemotherapeutics, vitamins, minerals, oligonucleotides, antisense nucleic acids and the like.

The transgenic animals of the present invention are also useful in determining the therapeutically effective dose of such therapeutic agents for use in treatment of animals afflicted with diabetes, obesity and cancers, in particular humans so afflicted. Until now, there have been no satisfactory animal models in which these diseases can be made to occur in a reliable and predictable fashion in a substantial proportion of animals in which these agents could be tested, and from which the gene at the mutant locus has been cloned.

The animals of the invention can also be used as a source of cells for cell culture. Cells from the animals may advantageously exhibit desirable properties as cultured cells. Where the promoter sequence controlling transcription of the gene sequence is inducible, cell growth rate and other culture characteristics can be controlled by adding or eliminating the inducing factor.

Obesity and non-insulin dependent diabetes are genetically inherited disorders in humans and mice. The obesity-associated diabetes of the $A^y$ and $A^{vy}$ mutant animals bears remarkable similarity to non-insulin dependent diabetes in obese humans. This is the first gene for genetic obesity to be cloned. Thus transgenic animals expressing the gene provides an animal model which is analogous to the human disease. Therefore the present invention provides transgenic animal model for studying diabetes, obesity and cancer in humans. Additionally, the present invention is useful for the molecular analysis of the biology, biochemistry and physiology of diabetes, obesity and cancer.

The present invention provides methods capable of detecting nucleic acid sequences associated with a gene in which expression of the gene product correlates with the development of diabetes, hyperamylinemia, neoplasms and obesity in animals, which comprises a) providing a test sample comprising nucleic acids isolated from a test animal specimen, b) providing at least one pair of single stranded oligonucleotide primers selected so that the oligonucleotides of the pair are complementary to the 5' abd 3' ends of one of double stranded cDNA nucleic acid sequences associated with the mRNA from the gene, c) combining the primer pair with the test sample under conditions such that the primer pair will hybridize sufficiently specifically to its nucleic acid sequence, d) treating the hybridized primers under conditions such that primer extension products are simultaneously synthesized for all sequences to which a primer is hybridized, e) repeating steps c) and d) until the nucleic acid sequences present are sufficiently amplified to be detected, and f) detecting the amplified nucleic acid sequences.

The particular uses and advantages of the invention include, but are not limited to: detection and cloning of the gene in which expression of the gene product correlates with the development of diabetes, hyperamylinemia, neoplasms and obesity in animals; detection of the Agouti gene and substantially homologous DNA sequences; detection of mutations in the gene; early detection of animals at risk of developing diabetes, obesity, neoplasms, and hyperamylinemia; and early treatment of afflicted animals.

The present invention is useful as a screening method for the detection of the gene in which expression of the gene product correlates with the development of diabetes, hyperamylinemia, neoplasms and obesity in animals, preferably the Agouti gene or substantially homologous genes in animals, preferably mammals. The inventive method utilizes amplification of nucleic acid sequences specifically associated with the gene, oligonucleotides or primer pairs, each specific for a nucleic acid sequence of the gene, provide the basis for amplification of the desired nucleic acid sequence. The inventive methods can be used to 1) identify the presence of the gene or 2) to screen for the presence of mutations in the gene.

The present invention also encompasses novel oligonucleotide probes useful in methods to amplify nucleic acid sequences, cloning of a gene or portions thereof and detecting the gene in which the expression of the gene product correlates with the development of diabetes hyperamylinemia, neoplasms and obesity in animals. Such probes are also useful in methods of diagnosing or prognosing such diseases. Of interest are probes which are capable of hybridizing to the Agouti gene or substantially homologous sequences or portions thereof; or a homologous or counterpart gene in animals, preferably mammals and of particular interest, the human counterpart gene to Agouti.

The present invention also contemplates kits which contain the reagents used in the practice of the inventive methods. The kits comprise, in a convenient package, the reagents used in screening for the gene or portions thereof, i.e., pairs of single stranded oligonucleotide primers selected so that the oligonucleotides of each pair are complementary to the 3' ends of one of double stranded nucleic acid sequence associated with and reagents for nucleic acid synthesis, whereby treatment of a test sample containing nucleic acid with the primers and the reagent results in hybridization of each primer pair to its target sequence and simultaneous amplification of the target sequences to which primers are hybridized.

It is an object of this invention to provide synthetic nucleic acid sequences capable of directing production of recombinant Agouti proteins, as well as equivalent natural nucleic acid sequences. Such natural nucleic acid sequences may also be isolated from a genomic library from which the gene capable of directing synthesis of the Agouti proteins may be identified and isolated.

The invention further relates to a method for detection of the Agouti gene or counterpart genes in animals in biological samples based on selective amplification of gene fragments utilizing primers derived from the Agouti genomic or cDNA or substantially homologous sequences.

The invention also relates to the use of single-stranded anti-sense poly- or oligonucleotides derived form the Agouti genomic cDNA or substantially homologous sequences to inhibit the expression of the Agouti gene or counterpart genes in animals as a means of inhibiting of modulating the diseases; obesity, diabetes, hyperinsulinemia and tumors.

The invention also relates to the method of preparing recombinant Agouti proteins derived from an Agouti genomic sequence by cloning the nucleic acid and inserting the cDNA into an expression vector and expressing the recombinant protein in a host cell.

The invention also relates to the use of the resultant recombinant proteins or portions thereof as diagnostic or therapeutic agents. Such therapeutic agents may be useful in treating diseases such as bulemia, anorexia and the like.

The present invention also encompasses methods of detecting the Agouti gene or counterpart gene product in biological samples. Such methods are useful for diagnosis of disease caused by the expression of the Agouti gene product, and for monitoring the progression of such disease. Such methods are also useful for monitoring the efficacy of therapeutic agents during the course of treatment of the disease in an animal, preferably a mammal.

Another aspect of the invention is a method for the manufacture of a recombinant protein which is encoded by a DNA sequence in which expression of the gene product is associated with the development of diabetes, obesity, hyperamylinemia and neoplasms in animals. In particular, this invention relates to a method for the manufacture of a recombinant protein encoded by the Agouti gene, counterpart genes, or by its functionally equivalent nucleic acid sequences, or analogs. It is a further object of this invention to provide a method for the manufacture of analogs of the protein which is encoded by DNA sequences in which expression of the gene product is associated with the development of diabetes, obesity, hyperamylinemia and neoplasms in animals.

The present invention also relates to antibodies, antigen-binding fragments of the antibodies, chimeric antibodies and their functional equivalents that react with a protein or fragment that is encoded by a gene in which expression of the gene product is associated with the development of the following diseases: insulin-independent diabetes, obesity, hyperamylinemia and neoplasms. The antibodies or their functional equivalents may be used as therapeutic agents in preventing or treating such diseases in animals. The antibodies or their functional equivalents may be used in immunoassays. Such assays are useful for monitoring the disease progression and are useful for monitoring the efficacy of therapeutic agents during the course of treatment of insulin-independent diabetes, obesity, hyperamylinemia and neoplasms.

Additionally, to achieve the objects and in accordance with the purposes of the present invention, pharmaceutical compositions containing, as an active ingredient, an isolated naturally occurring or recombinant protein or portion thereof encoded by a gene or functionally equivalent DNA sequences that encodes expression of the gene product promotes development of insulin-independent diabetes, obesity hyperamylinemia, and neoplasms.

Other features and advantages of the invention will be apparent from the description of the preferred embodiments thereof, and from the claims.

The contents of all cited patents and journal articles are incorporated herein by reference.

DESCRIPTION OF THE DRAWINGS

These and other objects, features, and many of the attendant advantages of the invention will be better understood upon a reading of the following detailed description when considered in connection with the accompanying drawings wherein:

FIG. 1A–1C. Identification of an Exon Near the Distal Inversion Breakpoint of Is1Gso. (A) Restriction map of a region of DNA that maps to the agouti locus and is associated with structural alterations in the extreme agouti mutations, Is1Gso and $a^{5MNU}$. The positions of two DNA probes that lie in close proximity to the distal inversion breakpoint in Is1Gso and the 2.8 kb deletion in $a^{5MNU}$ are indicated. R, EcoRI; B, BamHI; X, XbaI. (B) Identification of a segment of DNA near the distal inversion breakpoint of Is1Gso that is conserved in genomic DNA from several mammalian species. Probe A in (A) was $^{32}$P labeled and hybridized to EcoRI(R)- or PstI(P)- digested DNA from hamster, cat, and dog. The extensive smearing in hamster DNA is due to the presence of a rodent-specific repetitive element in probe A. The λHindIII molecular size standard is shown on the left in kilobases. (C) Identification of coding sequence near the distal inversion breakpoint of Is1Gso by Northern blot analysis. Probe B in (A) was $^{32}$P labeled and hybridized to poly(A)$^+$ RNA from wild-type skin of a day 4 neonate. The positions of the 28S and 18SrRNA subunits are indicated on the left. Higher molecular size smearing was due to the presence of moderately repetitive sequences in the probe.

FIG. 2. Shows Nucleotide and Predicted Amino Acid Sequence of the cDNA, identified as SEQUENCE ID NO. 11. The putative signal peptide sequence is underscored with a double line and the polyadenylation signal with a single line. The boxed region represents a highly basic domain that has the potential to be phosphorylated at a number of sites designated by PO$_4$. The asterisk denotes a potential N-linked glycosylation site, and cysteine residues are indicated by closed circles. Arrows delimit the boundaries of the four individual exons.

FIGS. 3A–3C. Shows Intro-Exon Structure of the Wild-Type Locus and Two Extreme Nonagouti Mutations. (A) Schematic representation of the genomic structure of the agouti gene in DNA from wild-type, Is1Gso, and $a^{5MNU}$ mice. The four exons are depicted as closed rectangles, and the introns and flanking sequences are shown as a solid line. The first exon, which is 72 bp long in the cDNA clone, is 8–10 bp longer at its 5' end based on RNAase protection experiments (data not shown). The 3' junction of the last exon corresponds to the 3' end of the cDNA clone, immediately upstream of the poly(A) tract. The precise location of each intron-exon junction was ascertained by identifying where genomic DNA sequences diverged from the cDNA sequence. At each splice junction, the genomic DNA sequence matched the canonical sequence for 5' splice donor and 3' splice acceptor sites (Mount, 1982 *Nucl. Acids Res.* 10:459–472) (data not shown). The open rectangle in the Is1Gso schematic represents genomic DNA from the Id gene in the opposite transcriptional orientation relative to agouti. The 2.8 kb intragenic deletion in the $a^{5MNU}$ mutation is depicted by a horizontal dashed line above the mutant locus, with the deleted region shown below the mutant locus. The positions of two probes (A and B) and the sizes of the EcoRI fragments they identify are shown. R, EcoRI; B, BamHI. (B) Identification of RFLVs specifically associated with the Is1Gso and $a^{5MNU}$ mutations. Wild-type (lane 1, C3H strain), Is1Gso homozygous (lane 2), and $a^{5MNU}$ homozygous (lane 3) genomic DNA was digested with EcoRI, blotted, and hybridized with a $^{32}$P-labelled fragment of DNA corresponding to probe A (lanes 1 and 2) or probe B (lane 3) in (A). The sizes of the DNA fragments detected by probes A and B are shown on the left in kilobases. (C) Nucleotide sequence of the distal inversion breakpoint of Is1Gso and the 5' and 3' deletion breakpoints of $a^{5MNU}$ compared with the wild type. The vertical bars indicate the positions of the DNA breakpoints. The lowercase nucleotides in Is1Gso represent sequence of the Id gene, and the horizontal lines in $a^{5MNU}$ represent deleted nucleotides.

FIG. 4. Northern Blot Analysis of Wild-Type (A/A) Neonatal Skin. The full-length cDNA clone (FIG. 2) was $^{32}$P labelled and hybridized to poly(A)$^+$ RNA (2.5 μg per lane) from skin of day 1–8 wild-type neonates (1–8) and day 6 W/W$^v$ neonates (W). RNA molecular size standards are shown on the left in kilobases. The filter was subsequently hybridized with a tubulin probe as a control to analyze the quantity and quality of the RNA in each lane.

FIGS. 9A-9B. Shows Molecular Analysis of the Size-Altered $A^y$ Transcript. (A) Schematic representation of the wild-type and lethal yellow ($\underline{A}^y$) transcripts produced by the agouti locus. Based on the analysis of cDNA clones, the $A^y$ transcript is identical to the wild-type transcript for the sequence derived from the second, third, and fourth exons. However, the 5' end of the second exon and the $\underline{A}^y$ transcript is flanked by a sequence that is different from the region corresponding to the first exon on the wild-type transcript. Moreover, our preliminary evidence suggests that this sequence unique to $A^y$ corresponds to the first noncoding exon (approximately 300 nt in length) of another gene. The genomic organization of the wild-type gene is shown above, with the four exons depicted as closed rectangles and the introns and flanking sequences shown as a solid line. B, BamHI; R, EcoRI. (B) Nucleotide sequence comparison of the wild-type and $\underline{A}^y$ cDNA clones, and comparison of the 5' end of the $\underline{A}^y$ cDNA with its corresponding genomic region. The sequence divergence point is positioned with a vertical line and corresponds to the junction between the first and second exons of the wild-type cDNA. Also, at this same junction point, the genomic sequence diverges from the $\underline{A}^y$ cDNA and is followed by a canonical 5' splice donor (Mount, 1982, ibid)

DETAILED DESCRIPTION OF THE INVENTION

Figure 5:
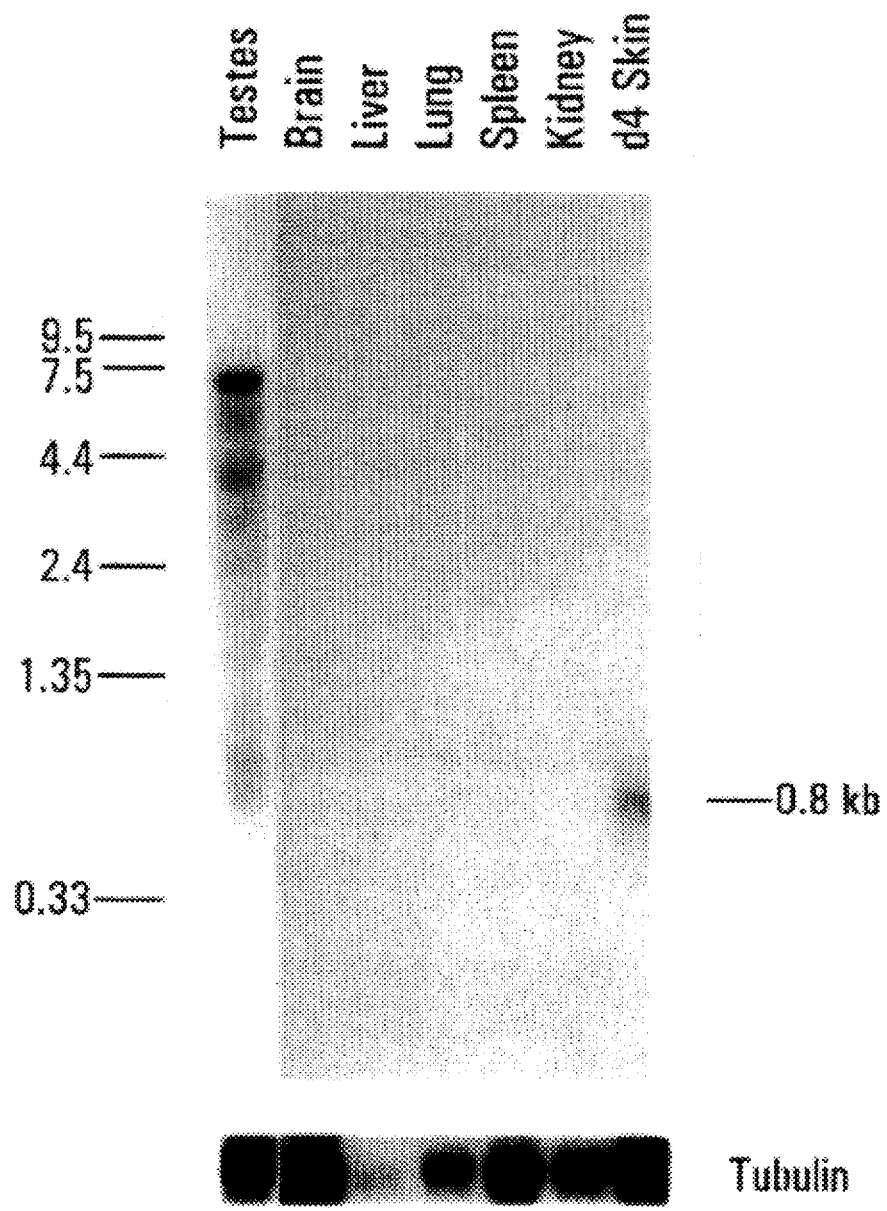
FIG. 5. Shows Northern Blot Analysis of Adult Tissues from Wild-type (A/A) Mice. The full-length cDNA clone was $^{32}$P labeled and hybridized to a variety of poly(A)$^+$ RNAs (2.5 μg per lane). RNA molecular size standards are shown on the left in kilobases. The filter was subsequently hybridized with a tubulin probe as a control to analyze the quantity and quality of the RNA in each lane.

The coat color of the wild-type mouse (and many other mammalian species) results from the formation of a subterminal yellow band in an otherwise black or brown hair shaft, a process that is regulated by the agouti locus in chromosome 2. Unlike many other regions of the mouse genome that regulate coat pigmentation, the agouti locus does not function in a melanocyte-specific manner, but rather elicits its response from within the follicular environment. Specifically, it appears that the agouti locus normally regulates the differential production of black and yellow pigments, by the melanocyte, through some direct or indirect form of intercellular communication.

Many spontaneous and induced mutations have been characterized at the agouti locus, and two of these in particular, $\underline{A}^y$ (lethal yellow) and Avy(viable yellow), are dominant and have relevance to human health. Both of these mutations exhibit a complex phenotype which includes hyperphagia, increased efficiency of food utilization, obesity, increased muscle mass and body size, hyperinsulinemia, insulin resistance, hyperamylinemia, impaired glucose tolerance, potentiation of responses to tumorigenic stimuli, and enhanced promotion and progression of transformed cells by factors associated with the obesity (reviewed in Wolff et al., 1986 *J. Hered.* 77:151–158; see also Wolff et al., 1987 *Carcinogen* 8:1889–1894; Gill and Yen, 1991, *Life Sciences* 48:703–710).

The present invention encompasses the cloning and identification of the agouti gene. This gene is approximately 18 kb in length, contains four exons, and gives rise to a 0.8 kb mRNA that has the potential to encode a 131 amino acid secreted protein (Woychik et al., 1990a, ibid; Bultman et al, 1991, ibid; Bultman et al., 1992). The present invention includes a polypeptide of approximately 131 amino acids in length and approximately 15,000 daltons in molecular size (FIG. 2) and functionally equivalent peptides or fragments thereof. This protein is secreted, since it contains a putative signal peptide at its N-terminus (FIG. 2). In addition, the molecule has several potential phosphorylation sites, a highly basic domain in the middle of the protein, and a cysteine-rich region near its C-terminus. Normally, as expected, the agouti mRNA is only produced within neonatal skin. However, the present invention has shown that the wild-type agouti gene product is ectopically overexpressed in mutants carrying the $\underline{A}^y$ or $\underline{A}^{vy}$ alleles (Bultman et al., 1992 *Cell* 71:1195–1204; Michaud et al., 1993 Genes and Development in press). It has been shown by the present invention that the ubiquitous expression of the normal agouti gene product correlates with the development of hyperamylinemia, neoplasms, insulin-independent diabetes and obesity and may be directly responsible for the dominant pleiotropic effects associated with $\underline{A}^y$ and $\underline{A}^{vy}$ and equivalent mutations in other animals, preferably mammals.

The cloning of the gene of the present invention, is the first and presently the only gene that has been cloned that is directly associated with an obesity/diabetes phenotype in an animal model. Other rodent models for obesity, including the ob/ob and db/db mouse mutants, along with the obese F(a/Fa) Zucker rat, have been studied extensively, and many investigators have been unsuccessful in cloning the genes associated with these mutants. The present methods and probes are useful in isolating and cloning analogous, or counterpart genes in other animals, especially mammals. Probes which hybridize to the mouse Agouti gene have been shown to hybridize to a unique human sequence with substantial homology to a portion of the mouse agouti gene. Such probes are useful for the isolation and cloning of the human counterpart agouti gene.

Based on studies of the $\underline{A}^y$ and $\underline{A}^{vy}$ mutants, ectopic expression of the agouti gene in muscle, liver and/or adipose tissue, the major targets insulin action, causes the insulin resistance, hyperinsulinemia, decreased glucose tolerance, and also the obesity. Transgenic mouse of the present invention are useful for evaluating the relationship of obesity to the development of insulin resistance associated with type II diabetes. To test whether expression of the agouti exclusively within adipose tissue in associated with just the obesity, and whether the expression within the liver and/or muscle exclusively caused the insulin-resistance, lines of transgenic mice that express the agouti gene specifically either in adipose tissue, or in the liver and/or muscle are used. This is done by placing the agouti gene under the control of muscle and/or liver, and fat-specific promoters/ enhancers. Transgenic mice carrying each of the different tissue-specific expression constructs are analyzed for expression compared to their non transgenic (littermates and A$^y$/–mice as controls).

The polymerase chain reaction ("PCR") has been a significant development in genetic analysis, allowing amplification of minute amounts of a specified gene sequence (U.S. Pat. No. 4,683,195; U.S. Pat. No. 4,683,202; U.S. Pat. No. 4,800,159; B. I. Eisenstein (1990) *The New England Journal of Medicine* 322:178–182; G. Schochetman et al. (1988) *The Journal of Infectious Diseases* 158:1154–1157), all incorporated herein by reference. In this method, a pair of single-stranded oligonucleotide primers, each complementary to sequences on opposite strands of the target DNA, are selected to encompass the target sequence to be amplified and define the two ends of the amplified stretch of DNA. After separating double stranded DNA and annealing the primers to the 3' end of the target sequence on each strand, two complementary second strands are synthesized by extension of the annealed primers using a DNA polymerase, i.e., a new single strand of DNA is synthesized for each annealed primer. These newly synthesized DNA's, as well as the original DNA sequence, can then be used for a second cycle of primer annealing and DNA synthesis. Accordingly, the desired target DNA sequence is amplified geometrically with each repetition of the cycle. Typically, within a few hours a target DNA sequence can be amplified 100,000 fold, particularly when automated methods are used to perform the cyclic reactions.

The polymerase chain reaction can also be used to specifically amplify only those target sequences which are expressed, i.e., those which are transcribed. To do so, mRNA is isolated and cDNA is made from the RNA using reverse transcriptase. The cDNA, which represents the expressed genes, is then used as target DNA in the PCR amplification reaction.

Because of its high sensitivity and specificity, PCR has been successfully used as a means for identifying microorganisms and viruses in the diagnosis of infections disease (B. I. Eisenstein (1990) *J. Infectious Diseases* 161: 595–602; L. Shih et al. (1990) *J. Medical Virology* 30:159–162; A. R. Lifson et al. (1990) *J. Infectious Diseases* 161:436–439; M. M. Anceschi et al. (1990) *J. Virological Methods* 28:59–66). PCR amplification has been used to detect changes in expression of the dTMP synthase gene (i.e., changes in the level of mRNA) associated with drug resistance in human tumors (K. J. Scanlon (1989) *J. Clinical Laboratory Analysis* 3:323–329; M. Kashani-Sabet et al. (1988) *Cancer Research* 48:5775–5778). PCR has also been used to analyze point mutations in HIV-1 reverse transcriptase which confer resistance to AZT (B. A. Larder et al. (1989) *Science* 246:1155–1158) and point mutations in the dihydrofolate reductasethymidylate synthase gene associated with pyrimethamine resistance in *Plasmodium falciparum* (A. F. Cowman et al. (1988) *PNAS* 85:9109–9113; J. W. Zolg et al. (1989) *Molecular and Biomedical Parasitology* 36:253–262; M. Tanaka et al. (1990) *Molecular and Biochemical Parasitology* 39:127–134; J. W. Zolg et al. (1990) *Molecular and Biochemical Parasitology* 39:257–266).

The present invention provides methods capable of detecting nucleic acid sequences associated with a gene in which expression of the gene product correlates with the development of diabetes, hyperamylinemia, neoplasms and obesity in animals which comprise a) providing a test sample comprising nucleic acid isolated from a specimen from a test animal, b) providing pairs of single stranded oligonucleotide primers selected so that the oligonucleotides of each pair are complementary to the 3' ends of one double stranded DNA target sequences associated with the gene, c) combining the primer pairs with the test sample under conditions such that each primer pair will hybridize sufficiently specifically to its target sequence, d) treating the hybridized primers under conditions such that primer extension products are simultaneously synthesized for all sequences to which a primer is hybridized, e) repeating steps c) and d) until the target sequences present are sufficiently amplified to be detected, and f) detecting the amplified target sequences.

The particular uses and advantages of the invention include, but are not limited to: detection and cloning of the gene in which expression of the gene product correlates with the development of diabetes, hyperamylinemia, neoplasms and obesity in animals, detection of the Agouti gene and substantially homologous DNA sequences; detection of mutations in the gene, early detection for animals at risk of developing diabetes, obesity, neoplasms, and hyperamylinemia, and early treatment of afflicted animals.

The present invention also relates to the use of single-stranded antisense poly-or oligonucleotides derived from sequences homologous to the Agouti cDNA to inhibit the expression of the Agouti gene product. These anti-sense poly-or oligonucleotides can be either DNA or RNA. The targeted sequence is typically messenger RNA and more preferably, a signal sequence required for processing or translation of the RNA. The antisense poly-or oligonucleotides can be conjugated to a polycation such as polylysine as disclosed in Lemaitre, M. et al. (1989) *Proc Natl Acad Sci USA* 84:648–652; and this conjugate can be administered to an animal preferably a mammal in an amount sufficient to hybridize to and inhibit the function of the messenger RNA to prevent expression of the Agouti gene product or counterpart gene product.

The present invention also relates to the cloning of the Agouti gene and the expression of the recombinant proteins and the cloning of the Agouti counterpart gene in animals, preferably mammals, particularly humans, using an expression system.

The present invention relates to isolated Agouti protein. Preferably, the Agouti protein of the present invention are substantially homologous to, and most preferably functionally equivalent to, the native Agouti protein. By "functionally equivalent" as used throughout the specification and claims, it is meant that the compositions are capable of promoting the development of diabetes, hyperamylinemia, tumors and obesity in animals. By "substantially homologous" as used throughout the ensuing specification and claims, is meant a degree of homology in the amino acid sequence to the native Agouti protein. Preferably the degree of homology is in excess of 50%, preferably in excess of 70%, of particular interest are proteins being at least of 90% homologous with the native Agouti protein.

In one embodiment the proteins or fragment thereof or analogs are those proteins or fragments thereof that are encoded by the Agouti gene. Of particular interest are proteins encoded by the Agouti gene depicted in FIG. 2, having sequence ID No.: 1.

It is contemplated that additions, substitutions or deletions of discrete amino acids or of discrete sequences of amino acids may be made to alter the biological activity of the Agouti proteins. The proteins may be naturally occurring or may be made by recombinant methods or chemically synthesized using methods known in the art for peptide synthesis.

The present invention is also a nucleic acid sequence which is capable of directing the production of the above-discussed Agouti protein or proteins substantially homologous to the Agouti proteins and variants thereof. One such nucleic acid sequence, designated C16, is depicted in FIG. 1 has SEQ ID NO.: 2. The deduced amino acid sequences encoded by Agouti gene starts at nucleotide 83 of SEQ. ID NO. 1 and extends to nucleotide 475.

Variations are contemplated in the DNA sequence which will result in a DNA sequence that is capable of directing production of analogs of the Agouti protein. It should be noted that the DNA sequence set forth above represents a preferred embodiment of the present invention. Due to the degeneracy of the genetic code, it is to be understood that numerous choices of nucleotides may be made that will lead to a DNA sequence capable of directing production of the instant Agouti proteins or their analogs. As such, DNA sequences which are functionally equivalent to the sequences set forth above or which are functionally equivalent to sequences that would direct production of analogs of the Agouti proteins produced pursuant to the amino acid sequence set forth above, are intended to be encompassed within the present invention.

The present invention includes a recombinant DNA method for the manufacture of Agouti proteins or fragments thereof. A natural or synthetic nucleic acid sequence may be used to direct production of the Agouti proteins. In one embodiment of the invention, the method comprises:

(a) preparation of a nucleic acid sequence capable of directing a host organism to produce a protein encoded by the Agouti gene or substantially homologous or counterpart gene;

(b) cloning the nucleic acid sequence into a vector capable of being transferred into and replicated in a host organism, such vector containing operational elements for the nucleic acid sequence;

(c) transferring the vector containing the nucleic acid and operational elements into a host organism capable of expressing the protein;

(d) culturing the host organism under conditions appropriate for amplification of the vector and expression of the protein; and (e) harvesting the protein.

In another embodiment of the invention, the method for the recombinant DNA synthesis of a protein encoded by nucleic acid sequences of the Agouti gene or substantially homologous or counterpart gene, comprises:

(a) culturing a transformed or transfected host organism containing a nucleic acid sequence capable of directing the host organism to produce a protein, under conditions such that the protein is produced, said protein exhibiting substantial homology to a native Agouti protein having the amino acid sequence according to SEQ ID NO. 1 or fragments or analogs thereof.

The vectors contemplated for use in the present invention include any vectors into which a nucleic acid sequence as described above can be inserted, along with any preferred or required operational elements, and which vector can then be subsequently transferred into a host organism and replicated in such organism. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

In construction of the cloning vector of the present invention, it should additionally be noted that multiple copies of the nucleic acid sequence and its attendant operational elements may be inserted into each vector. In such an embodiment, the host organism would produce greater amounts per vector of the desired Agouti protein. The number of multiple copies of the DNA sequence which may be inserted into the vector is limited only by the ability of the resultant vector due to its size, to be transferred into and replicated and transcribed in an appropriate host microorganism.

In another embodiment, restriction digest fragments containing a coding sequence for Agouti protein or substantially homologous protein or analogs thereof can be inserted into a suitable expression vector that functions in prokaryotic or eukaryotic cells. By suitable is meant that the vector is capable of carrying and expressing a complete nucleic acid sequence coding for the Agouti proteins or substantially homologous proteins or analogs thereof. Preferred expression vectors are those that function in a eukaryotic cell. Examples of such vectors include but are not limited to vaccinia virus vectors, adenovirus or herpesviruses, preferably the baculovirus transfer vector, pBlueBac.

In yet another embodiment, the selected recombinant expression vector may then be transfected into a suitable eukaryotic cell system for purposes of expressing the recombinant protein. Such eukaryotic cell systems include but are not limited to cell lines such as HeLa, MRC-5, SF9 insect cells or Cv-1.

The expressed recombinant protein may be detected by methods known in the art which include Coomassie blue staining and immunoassays such as Western blotting using sera containing anti-Agouti, antibody or by using Southern or Northern blots using labeled oligonucleotide probes.

In a further embodiment, the recombinant protein expressed by the host cells can be obtained as a crude lysate or it can be purified by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the recombinant protein may be purified by passage through a column containing a resin which has bound thereto antibodies specific for the Agouti protein or substantially homologous proteins or analogs thereof.

The recombinant Agouti proteins, and substantially homologous proteins and analogs of the invention can be used as a therapeutic agent. The therapeutic agent may be a cell, cell lysate from cells transfected with a recombinant expression vector or a culture supernatant containing the expressed protein. Alternatively, the therapeutic agent is a partially or substantially purified recombinant protein.

While it is possible for the protein to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. Additional pharmaceutical methods may be employed to control the duration of action. Controlled release preparations may be achieved through the use of polymer to complex or absorb the proteins or their derivatives.

The proteins of the present invention may be supplied in the form of a kit, alone, or in the form of a pharmaceutical composition as described above.

The administration of the protein or peptides of the present invention may be for therapeutic purpose. The administration of the protein or peptides serves to prevent or attenuate any subsequent disease development associated with the overexpression of the Agouti gene product in a mammal. When provided therapeutically, the protein or peptide is provided at (or shortly after) any symptom of disease caused by expression of the Agouti gene product or substantially homologous gene product. The therapeutic administration of the immunogen serves to attenuate the disease. It is anticipated that small peptides homologous to a portion of the Agouti gene product may inhibit the function of the full length gene product.

In addition to use as a therapeutic agent, the compositions can be used to prepare antibodies to Agouti protein. The antibodies also can be used directly as therapeutic agents. To prepare antibodies, a host animal is immunized using the Agouti protein or substantially homologous protein or fragment thereof. The protein or fragments thereof may or may not be bound to a carrier to make the protein immunogenic. Examples of such carrier molecules include but are not limited to bovine serum albumin (BSA), keyhole limpet hemocyanin (KLH), tetanus toxoid, and the like. The protein can be administered by any route appropriate for antibody production such as intravenous, intraperitoneal, intramuscular, subcutaneous, and the like. The protein may be administered once or at periodic intervals until a significant titer of anti-Agouti antibody is produced. The host serum or plasma is collected following an appropriate time interval to provide a composition comprising antibodies reactive with the protein or portions thereof. The gamma globulin fraction or the IgG antibodies can be obtained, for example, by use of saturated ammonium sulfate or DEAE Sephadex, or other techniques known to those skilled in the art.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80:15553, all incorporated herein by reference).

General reviews of "humanized" chimeric antibodies are provided by Morrison S., 1985 Science 229:1202 and by di et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedleret al. 1988 J. Immunol. 141:4053, all incorporated herein by reference).

The antibodies or antigen binding fragments may also be produced by genetic engineering. The technology for expression of both heavy and light cain genes in E. coli is the subject the PCT patent applications; publication number WO 901443, WO901443, and WO 9014424 and in Huse et al., 1989 Science 246:1275–1281.

It may be preferable to use monoclonal antibodies. Monoclonal anti-Agouti antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., NY, N.Y., pp. 56–97). To produce a human—human hybridoma, a human lymphocyte donor is selected. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human—human hybridomas. Primary in vitro immunization with peptides can also be used in the generation of human monoclonal antibodies.

Antibodies secreted by the immortalized cells are screened to determine the clones that secrete antibodies of the desired specificity. Cells producing antibodies of the desired specificity are selected.

Antibodies are useful in immunoassays for diagnosing or prognosing of diseases associated with expression of the Agouti gene product.

Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Methods in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art. (Oellerich, M. 1984, *J. Clin. Chem. BioChem.* 22: 895–904) Biological samples appropriate for such detection assays include, but are not limited to, tissue biopsy extracts, cerebrospinal fluid, pleural fluid, urine and the like.

In one embodiment, test sample is reacted with a solid phase reagent having surface-bound anti-Agouti antibodies. The solid surface reagent can be prepared by known techniques for attaching protein to solid support material. These attachment methods include non-specific adsorption of the antibody to the support or covalent attachment of the antibody to a reactive group on the support. After reaction of the test sample with anti-Agouti antibody, unbound sample components are removed by washing and the antigen-antibody complex is reacted with a labelled secondary antibody. The label may be an enzyme which is detected by incubating the solid support in the presence of a suitable fluorimetric or calorimetric reagent. Other detectable labels may also be used, such as radiolabels or colloidal gold, and the like.

The Agouti antibody and functional equivalents may be prepared in the form of a kit, alone, or in combinations with other reagents such as secondary antibodies, for use in immunoassays.

The above described antibodies and antigen binding fragments thereof may be supplied as a pharmaceutical composition for in vivo use. The antibodies may be used for therapeutic uses, diagnostic use in immunoassays or as an immunoaffinity agent to purify Agouti proteins or substantially homologous proteins or fragments thereof as described herein.

EXAMPLE 1

Animals

All mice were maintained at the Oak Ridge National Laboratory, including the SB B+T stock, derived from a mutation that arose spontaneously at the Oak Ridge National Laboratory in an SEC/E×C57BL/E mating.

EXAMPLE 2

DNA Isolation and Southern Blot Analysis

Genomic DNA (ug) was digested with restriction enzymes, electrophoresed through agarose gels, and blotted to GeneScreen (DuPont) utilizing standard procedures (Ausubel et al., 1988; Sambrook et al., 1989). Radiolabeled hybridization probes were prepared with the random hexamer labeling technique (Feinberg and Vogelstein, 1984 *Anal. Biochem.* 137:226–267). Prior to hybridization, probe 1.5 was reassociated with sheared, genomic mouse DNA to prevent the hybridization of repetitive sequence (Sealey et al. 1985 *Nucl. Acids Res.* 13:1905–1922). Posthybridization filter washing was conducted under high stringency (0.2× SSC, 0.1% SDS at 68° C.) or reduced stringency (0.2×SSC, 0.1% SDS at 50° C.) conditions for membranes containing DNA from mice or other mammalian species, respectively.

EXAMPLE 3

RNA Preparation and Northern Blot Analysis

Total RNA was prepared using the guanidine isothiocyanate procedure (Ausubel et al. 1988 *Current Protocols in Molecular Biology*, New York, N.Y., John Willey & Sons), enriched for poly $(A)^+$ RNA using an oligo (dT)-cellulose column (Aviv and Leder, 1972 *Proc. Natl. Acad. Sci. USA* 69:1408–1412), electrophoresed through formaldehyde gels, and blotted to GeneScreen (DuPont) utilizing standard procedures known in the art. The membrane was hybridized and washed under high stringency conditions as described above for Southern blot analysis.

EXAMPLE 4

Isolation of cDNA

Poly $(A)^+$ RNA was prepared from day 5 neonatal skin (C3H strain) or adult $A^y$ 1s1Gso kidney or testis as described above, and double-stranded cDNA was subsequently prepared with reverse transcriptase using standard procedures (Ausubel et al. 1988, ibid; Sambrook et al. 1989 *Molecular Cloning: A Laboratory Manual, Second Edition*, Cold Spring Harbor, N.Y.; Cold Spring Harbor Laboratory Press. After the addition of EcoRI linkers, the cDNA was ligated into the λgt10 vector (Stratagene), packaged in vitro, and screened with probe B (FIG. 1A) (for the neonatal skin cDNA library) or the wild-type cDNA clone (for the $A^y$/1s1Gso cDNA libraries) using standard procedures (Ausubel et al. 1988, ibid; Sambrook et al. 1989, ibid). Positive clones were purified using conventional methods and subcloned into pGEM (Promega) or pBluescript (stratagene) for further analysis.

EXAMPLE 5

Isolation of Genomic Clones

Genomic spleen DNA from the strain 129/RI was partially digested with Sau3A and size fractionated on a 10%–40% sucrose gradient (Sambrook et al., 1989, ibid). Fractions containing 35–45 kb fragments were ligated into the cosmid vector c2RB (Bates and Swift, 1983 *Gene* 26:137–146), packaged in vitro, and screened using standard procedures (Ausubel et al. 1988, ibid; Sambrook et al. 1989, ibid). Utilizing the cDNA clone as a probe, cosmid subfragments were isolated and subcloned into pGEM (Promega) or pBluescript (Stratagene) by standard procedures.

EXAMPLE 6

DNA Sequencing

Genomic and cDNA clones were sequenced by the Sanger dideoxynucleotide method (Sanger et al., 1977 *Proc. Natl. Acad. Sci. USA* 74:5463–5467) using T7 DNA polymerase (US Biochemical) (Tabor and Richardson, 1987 *Proc. Natl. Acad. Sci. USA* 84:4767–4771). Analysis of the DNA sequence was performed using the University of Wisconsin Genetics Computing Group sequence analysis programs (Devereux et al. 1984 (*Nucl. Acids Res.* 12:387–395).

EXAMPLE 7

Isolation of a cDNA Clone and Genomic Structure of the a Locus

Having established from previous work that the distal inversion breakpoint of Is1Gso likely lies within the agouti locus (Bultman et al. 1991, ibid), we initiated a search to find an locus exon. Interspecific hybridizations identified a region of DNA near the distal inversion breakpoint of Is1Gso (FIG. 1A) that is conserved in a number of mammalian species (FIG. 1B). This evolutionarily conserved region was subsequently shown to be expressed based on its ability to hybridize to a 0.8 kb transcript in RNA prepared from neonatal skin of wild-type animals (FIG. 1C). Neonatal skin cDNA libraries were subsequently prepared and screened with probe B (FIG. 1A), resulting in the identification of several clones, one of which contained the entire coding region and is nearly full length. The total size of this cDNA clone is 800 bp, which is comparable with the size of the RNA seen on Northern blots. The complete nucleotide sequence is 692 bp, excluding the poly(A) tract (FIG. 2). The cDNA contains an open reading frame extending from nucleotide 83 through 478, beginning with an ATG codon flanked by sequence that is in agreement with consensus sequence for translation initiation (Kozak, M. 1987 Nucl. Acids Res. 15:8125–8148). The hexanucleotide AATAAT is present within the 3' untranslated sequence immediately preceding the poly(a) tract and probably represents the polyadenylation signal of the gene (Sheets, M. D. et al. 1990 Nucl. Acids Res. 18:5799–5805; Dürkop, H. et al. 1992 Cell 68:421–427).

The translation product deduced from the open reading frame is 131 amino acids in length with a molecular size estimated to be 15,000 daltons (FIG. 2). Searches of the NBRF and SWISSPROT data bases using the algorithm FASTA (Pearson and Lipman, 1988 Proc. Natl. Acad. Sci. USA 85:2444–2448) failed to identify any proteins with significant sequence homology. The N-terminus may comprise a signal peptide, since it is hydrophobic (Kyte and Doolite, 1982 J. Mol. Biol. 157:105–132) and includes a possible cleavage site after residue 22 (von Heijne, G. 1986 Nucl. Acids Res. 14:4683–4690). A highly basic domain containing 16 lysine or arginine residues in a stretch of 29 amino acids is present in the center of the predicted protein and is followed by a polyproline stretch. At the carboxyl terminus, 10 of the final 40 amino acids are cysteines, and in four instances, cysteine residues are spaced 6 amino acids apart. In addition, one putative N-linked glycosylation site and nine potential serine/threonine kinase phosphorylation sites are present within the predicted protein, five of which lie within the highly basic domain.

To educate the intron-exon composition of the gene corresponding to the cDNA clone presented in FIG. 2, overlapping genomic clones were isolated and characterized utilizing the cDNA clone as a probe. Comparison of the structure of the genomic and cDNA clones revealed that the gene contains four exons (FIG. 3A). The first exon of the cDNA is 72 bp in length and is composed entirely of 5' untranslated sequence. The first intron is approximately 11.5 kb in length and is followed by the second (170 bp), third (65 bp), and fourth (385 bp) exons, which are separated by introns of 2.5 kb and 2.8 kb, respectively (FIG. 3A). The gene spans an overall distance of 18 kb.

EXAMPLE 8

Wild-Type Pattern of Expression

Utilizing the cDNA clone as a probe, poly(a)$^+$ RNA from the skin of newborn wild-type mice was examined at daily intervals and was shown to express the 0.8 kb transcript throughout early postnatal development; the level of expression appeared to be greatest, however, during days 2–7 (FIG. 4). To determine whether the 0.8 kb transcript is expressed exclusively by melanocytes within the hair follicle, W/W$^v$ mice were examined because they lack hair bulb melanocytes owing to a defect in the c-kit gene (Geissler, et al. 1988 Cell 55:185–192). The 0.8 kb transcript was shown to be present in neonatal skin from W/W$^v$ mice (FIG. 4), indicating that it is expressed by the follicular environment.

Poly(A)$^+$ RNA was also analyzed from a variety of wild-type adult issues (FIG. 5). Based on Northern blot analysis and RNAase protection assays, it was determined that none of the testis-specific transcripts were expressed in neonatal skin (data not shown). Therefore, it is unlikely that the testis-specific transcripts are playing any role in a locus function.

EXAMPLE 9

Changes in Gene Structure and Expression in Several Agouti Locus Mutations

In an attempt to provide evidence that the gene we have characterized is in fact the agouti gene, we tested whether it is structurally altered in agent-induced or spontaneous a locus mutations. First of all, utilizing two probes from with the 5.5 kb wild-type EcoRI fragment at the 3' end of the gene, mutant locus-specific restriction fragment length variants (RFLVs) of 7.5 kb and 3.5 kb were detected for the agent-induced extreme nonagouti mutations Is1-Gso and a$^{5MNU}$ (see FIG. 3B), respectively. Additional experiments revealed that the 7.5 kb RFLV arises from a DNA structural alteration at the distal inversion breakpoint of Is1Gso, which causes the 5' half of the gene to be juxtaposed with a portion of the ld gene (Maas, R. L., et al. 1990 Nature 346:853–855; Woychik, R. P. et al. 1990b Nature 346:850–853) in the opposite transcriptional orientation (see FIGS. 3A and 3B). For a$^{5MNU}$, the 3.5 kb RFLV is due to an intragenic deletion encompassing 2.8 kb of genomic DNA, which includes the third exon (see FIGS. 3A and 3B). The distal inversion breakpoint of Is1Gso and the deletion breakpoint of a$^{5MNU}$ have also been characterized by nucleotide sequence analysis (see FIG. 3C).

Figure 6A:
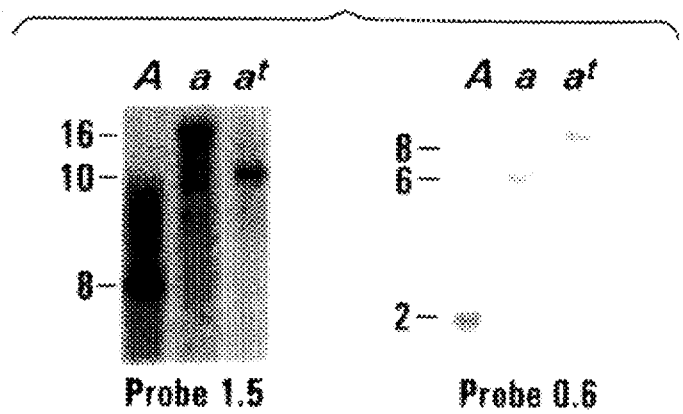
FIGS. 6A–6B. Shows the Identification of DNA Structural Alterations Associated With the a and a$^t$ Alleles. (A) Wild-type (A, C3H strain), nonagouti (a, C57BL/E strain), and black-and-tan (a$^t$, SB B+T stock) genomic DNA was digested with BamHI or BglII, blotted, and hybridized with a $^{32}$P-labeled fragment of DNA corresponding to probe 1.5 (BamHI digest) or probe 0.6 (BglII digest), shown as thick horizontal lines in the illustration of the wild-type allele in (B). The size of the DNA fragments detected by the two probes are shown in the left margin in kilobases. The SB B+T mutation arose in a cross between the strains SEC/E and C57BL/E, both of which are nonagouti (a/a) homozygotes and display a 16.0 kb BamHI fragment with probe 1.5 and a 6.0 kb BglII fragment with probe 0.6, although only the C57BL/E result is shown. The parental strain from which the original nonagouti a mutation rose is not known; however, two wild-type inbred strains, FVB/N and 101, were analyzed in addition to C3H, and all displayed the wild-type pattern illustrated for C3H. (B) Schematic representation of 5' end of the gene shown in FIG. 3 from wild-type (A), nonagouti (a), and SB B+T mutant (a$^t$) mice. The first exon is shown as a closed rectangle, and the bold horizontal line represents the 5' flanking sequence and portion of the first intron. Probe 1.5 detects a 8.0 kb fragment in wild type, and RFLV fragments of 16.0 kb and 10.0 kb in the a and a$^t$ mutant alleles, respectively. Probe 0.6 detects a 2.0 kb wild-type fragment and RFLV mutant allele-specific fragments of 6.0 kb in a and 8.0 kb in a$^t$. These RFLVs are due to the presence of at least 11 kb (a) or 5.5 kb (a$^t$) of additional sequence in the mutant alleles within a highly localized 700 bp region on the wild-type DNA between BglII and EcoRI sites. The insertions for each allele have not yet been cloned and mapped, and therefore are depicted by vertical bars with open parentheses at the end. B, BamHI; R, EcoRI, Bg, BglII.
Figure 6B:
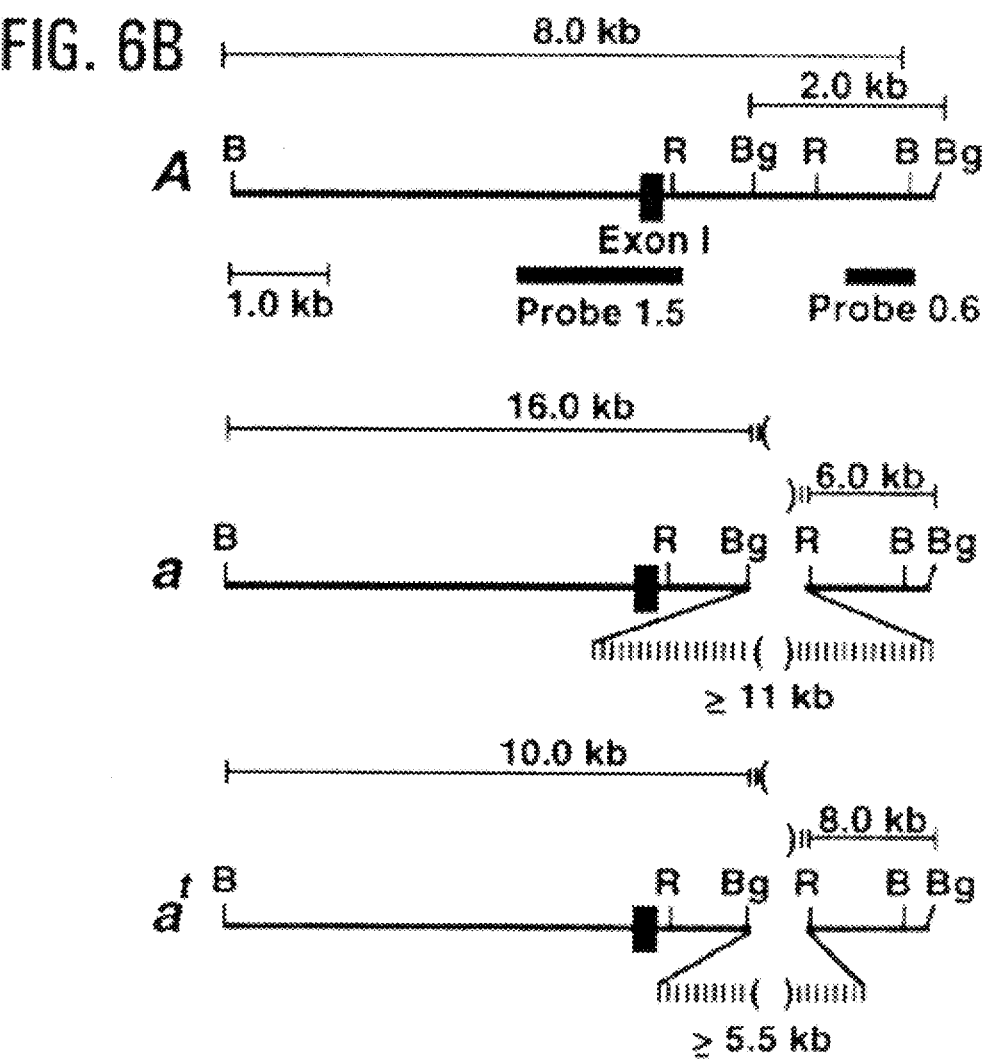

In additional experiments, we also analyzed the molecular structure of the original nonagouti mutation (a) and a black-and-tan (a$^t$) allele called SB B+T that arose spontaneously in a cross of the SEC/E and C57BL/E inbred lines at the Oak Ridge National Laboratory. For these experiments, probes containing either the first exon (probe 1.5) or a portion of the first intron (probe 0.6) each detected a distinct mutant locus-specific RFLV associated with the a and a$^t$ mutations (FIGS. 6A and 6B). Based on this analysis, it appears that each of these mutant alleles contains a structural alteration caused by the presence of extra DNA (at least 11 kb or 5 kb for the a or a$^t$ mutations, respectively) within a region corresponding to a 700 bp BglII-EcoRI fragment within the first intron of the wild-type gene (FIG. 6B).

Figure 7:
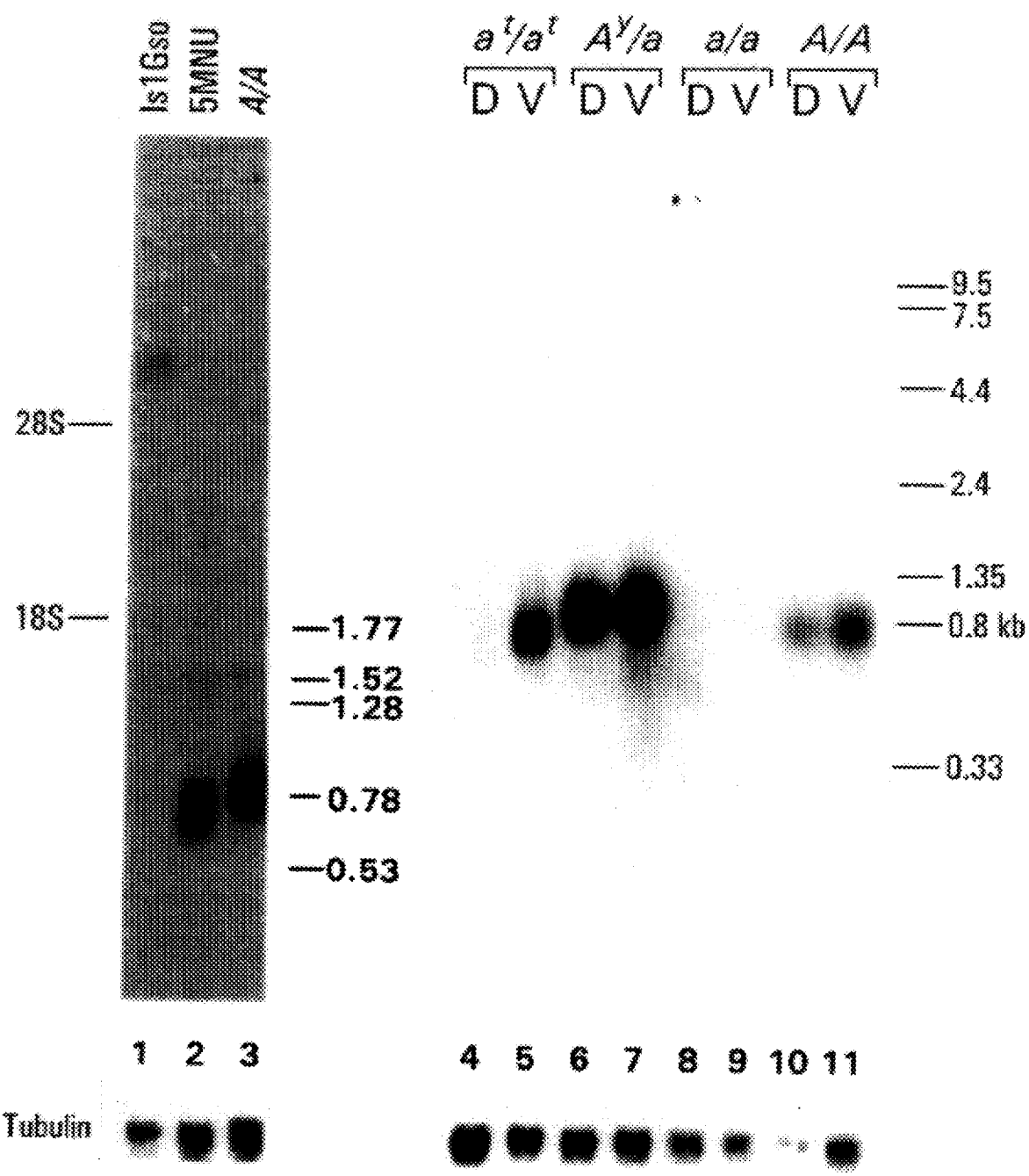
FIG. 7. Northern Blot Analysis of Neonatal Skin from Several Agouti Locus Mutants. The full-length cDNA clone (FIG. 2) was $^{32}$P labelled and hybridized to poly(A)$^+$ RNA (2.5 μg per lane) from neonatal skin of spontaneous or agent-induced a locus mutations. RNA molecular size standards (in kilobases) and the positions of the 28S and 18S rRNA subunits are shown. The filter was subsequently hybridized with a tubulin probe as a control to analyze the quantity and quality of the RNA in each lane. D, skin derived from the dorsal surface of neonates; V, skin derived from the ventral surface of neonates; Is1Gso, day 4 Is1Gso homozygote; 5MNU, day 5 $\underline{a}^{5MNU}$ homozygote; A/A, day 5 wild type; $\underline{a}^t/\underline{a}^t$, day 5 black-and-tan; $A^y/\underline{a}$, day 6 lethal yellow heterozygote; a/a, day 6 nonagouti (C57BL/10).

As expected, the DNA structural alterations in Is1Gso, a$^{5MNU}$, a, and a$^t$ cause detectable changes in the expression of the gene. Production of the 0.8 kb transcript is absent in neonatal skin from Is1Gso homozygotes and is replaced by a low abundance 8.0 kb transcript that likely arises from cryptic elements on the rearranged gene segments (FIG. 7, lane 1). In neonatal skin from a$^{5MNU}$ homozygotes, a transcript is present at wild-type levels, but is decreased in size to an extent that is consistent with a deletion of the third exon of the gene (FIG. 7, compare lanes 2 and 3). Deletion of the third exon results in the removal of 21 codons and the introduction of a frame shift within the last exxon (see FIG. 3A). The original nonagouti mutation in C57BL mice does not express the 0.8 kb transcript (FIG. 7, lane 8 and 9). In black-and-tan neonates, the 0.8 kb transcript is absent in skin derived from the black, dorsal surface, but is overexpressed in skin derived from the yellow, ventral surface (FIG. 7, lanes 4 and 5). Control samples from wild-type (A/A) mice showed similar levels of expression of the 0.8 kb transcript in the dorsal and ventral surfaces (FIG. 7, lanes 10 and 11). Notably, $\underline{A}^y$ is associated with a marked increase in expression of a larger than normal transcript (FIG. 7, lanes 6 and 7).

EXAMPLE 10

Deregulated Expression in Lethal Yellow Heterozygotes

Figure 8:
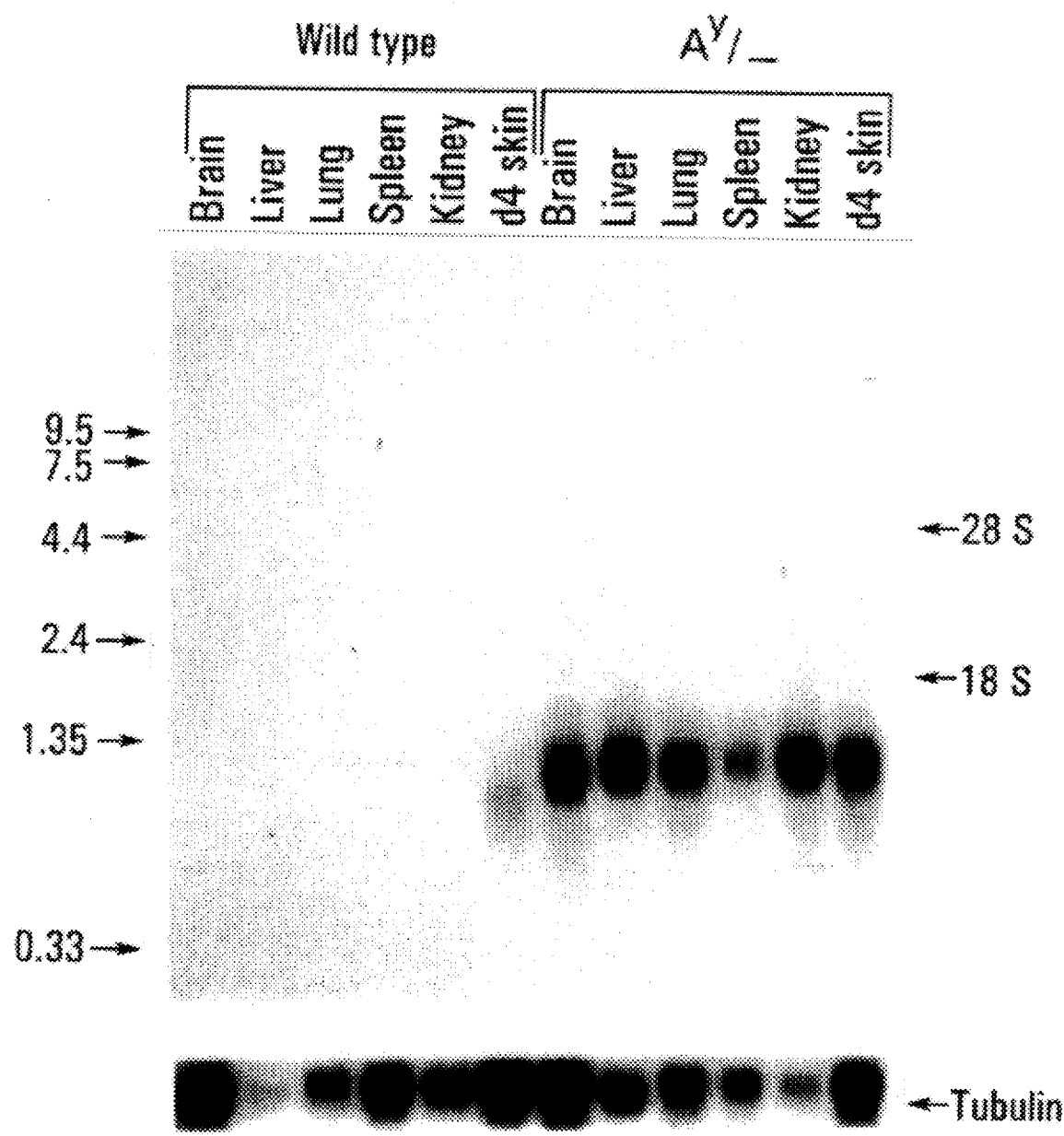
FIG. 8. Shows Northern Blot Analysis of Adult Tissues from Wild-Type and Lethal Yellow Heterozygotes. The full-length cDNA clone (FIG. 2) was $^{32}$P labelled and hybridized to poly(A)$^+$ RNA (2.5 μg per lane) from adult tissues or neonatal skin of wild-type or $\underline{A}^y$/-mutant animals. RNA molecular size standards are shown on the left in kilobases, the positions of the 28S and 18S rRNA subunits are indicated on the right. The filter was subsequently hybridized with a tubulin probe as a control to analyze the quantity and quality of the RNA in each lane. $\underline{A}^y$/-, $\underline{A}^y$ heterozygotes with genotypes of $\underline{A}^y/\underline{a}$ and $\underline{A}^y/\underline{a}^e$ were used in this analysis; d4 skin, day 4 postnatal skin; d6 skin, day 6 postnatal skin.

Lethal yellow ($\underline{A}^y$) heterozygotes display a number of pleiotropic effects, including pronounced obesity, a diabetes like condition, and a propensity to develop a variety of spontaneous and induced neoplasms in the adult. To examine the molecular defect associated with $\underline{A}^y$ allele more precisely, a number of adult tissues from lethal yellow heterozygotes were analyzed for expression of the gene we have characterized. In striking contrast with wild-type mice, where expression is restricted to testis and neonatal skin, $\underline{A}^y$ animals overexpressed a size-altered transcript in every tissue examined (FIG. 8).

To characterize the nature of the increased size of the $\underline{A}^y$ transcript, an adult kidney and testis cDNA library was prepared from lethal yellow heterozygotes and screened using the wild-type cDNA clone as a probe. Analysis of several $\underline{A}^y$ cDNA clones indicated that the first exon of the agouti gene has been replaced by novel sequence on the $\underline{A}^y$ transcript, whereas the second, third, and fourth agouti exons, which contain the entire coding region, remain intact (FIG. 9A). Moreover, characterization of the genomic region flanking the novel sequence revealed a potential intron-exon consensus sequence precisely at the point of divergence with cDNA clone (FIG. 9B). This result strongly suggests that the altered size $\underline{A}^y$ transcript arises through a mechanism that involves splicing of the region of novel sequence to the second exon of the gene.

EXAMPLE 11

Promoter/Enhancers for Tissue-Specific Gene Expression in Muscle

Several promoter/enhancers that drive tissue-specific gene expression in muscle, adipose tissue, and liver have been identified. The following promoter/enhancers, have been extensively characterized, shown to drive optimal levels of tissue specification transcription in transgenic mice, and are available as published plasmid expression cassettes. An expression cassette contains the regulatory elements necessary for expression of an inserted gene. These include a promotor and polyadenylation site and if necessary an enhancer element. For muscle specific expression, the rat myosin light chain is used. (MLC1/3) gene promoter/enhancer from clone pMLC1CAT920, which has been used previously to drive high level expression of a chloramphenicol acetyltransferase (CAT) transgene exclusively in skeletal muscle of transgenic mice (Rosenthal et al., 1989 *Proc. Natl. Acad. Sci. USA* 86:7780–7784). In this pUC9-based clone, 1.5-kbHindIII fragment containing the MLC1 promoter, cap site, and 105 bp of 5' untranslated sequence is fused to a 1.6-kbHindIII-BamHI fragment containing the CAT gene with the small intron and polyadenylation site of the SV40 t antigen, which is followed (3') by a 920-bp BamHI fragment containing a strong, muscle specific enhancer element that is normally located >24 kb downstream of the MLC 1 transcription start site. The CAT gene is excised exercised from this clone by HindIII-BamHI digestion and the full length cDNA as depicted in FIG. 2 (cDNA16), substantially homologous sequences, analogs or functionally equivalent sequences is inserted into this site. This MLC1 promoter-agouti-MLC1 enhancer clone is linearized and microinjected into the pronuclei of fertilized eggs, and transgenic lines are produced.

EXAMPLE 12

Promotor/Enhancers for Tissue-Specific Gene Expression in Adipose Tissue

To express the gene of the present invention exclusively in adipose tissue, the murine adipocyte P2 (aP2) gene promoter/enhancer contained in clone 5.4aP2CAT is used, which has been shown to direct very high level CAT expression specifically to adipose tissue in transgenic mice (Ross et al. 1990 *Proc. Natl. Acad. Sci. USA* 87:9590–9594). This clone consists of an upstream fragment (−5.4 kb to +21 bp relative to the transcription start site) of the aP2 gene, that contains the promoter and a strong adipocyte-specific enhancer (located in the −5.4 kb to −4.9 kb DNA segment), linked to the CAT gene with the small intron and polyadenylation site of the SV 40 t minigene. The CAT gene is replaced by the agouti minigene paP2Pe-agouti-SVpA to generate the expression construct. Specifically, a 1.1 kb HindIII-ClaI fragment containing the agouti cDNA and SV40 polyA signal from the pBAP-a-SVpA plasmid is cloned into the NotI site of the p-5.4aP2 plasmid using NotI linkers (clone paP2PE-a-SVpA). A 6.6 kb KpnI-SacII fragment containing the aP2 promoter-agouti expression cassette is isolated from the vector sequences in paP2Pe-agouti-SVpA and is used for microinjection. In this case, an ~1 kb agouti transcript is produced from this expression cassette, which is several hundred nucleotides larger than the endogenous agouti transcript.

EXAMPLE 13

Promoter/Enhancers for Tissue-Specific Gene Expression in Liver

To achieve liver-specific expression of the agouti gene, the mouse albumin gene promoter/enhancer from the clone Nb.3alb-HGH is used, which has been used successfully to achieve liver-specific expression of the human growth hormone (hGH) gene in transgenic mice at levels near that of endogenous albumin gene expression (Pinkert et al., 1987 *Genes Dev. 1:268–276*). This clone contains an upstream (−10.4 to −8.5 kb) albumin enhancer-containing fragment, linked to the liver-specific albumin promoter, which is fused to the hGH structural gene. The hGH gene is replaced with the agouti minigene and transgenic mice are generated as described above. Specifically, a 1.1 kb SalI fragment containing the agouti cDNA and SV40 polyadenylation signal is cloned into the SalI site of the NB-0.3alb plasmid just 3' to the albumin enhancer/promoter. After CsCl purification of the plasmid, a 3.5 kb SacI-KpnI fragment containing the expression cassette is isolated away from the vector sequences and used for microinjection. Expression of the agouti cDNA from this cassette produces a ~1 kb transcript, which is several hundred nucleotides longer than the endogenous agouti transcript.

Transgenic mice that express agouti either in liver, muscle, or fat, establishes whether expression in the liver/ muscle is sufficient for the insulin resistance without obesity, and whether expression exclusively in adipose tissue is sufficient to cause obesity without the diabetes. In the event that expression in both the liver/muscle and adipose tissue are both necessary for either the insulin resistance and/or obesity, the different individual transgenic lines are intercrossed to generate mice expressing agouti in difference combinations of two tissues (i.e., liver and muscle, muscle and fat, and liver and fat). These mice in turn, are mated to mice expressing agouti solely in the third remaining tissue to generate transgenic mice that express agouti in all three tissues. This establishes the contribution of each tissue necessary for the obesity and insulin resistance traits. Additionally, the transgenic lines that express the agouti gene in the liver should yield information regarding the role of the agouti gene product in the development of liver tumors.

EXAMPLE 14

Promoter/Enhancers for Tissue-specific Gene Expression the Pancreas

For expression in the pancreas the islet cell specific promoter from the rat insulin gene is utilized. Obesity/diabetes effects associated with the ectopic expression of the agouti gene in the beta-cells of the pancreas are analyzed. The resulting transgenic animals are used to study the expression of agouti in the pancreas to determine if this causes an increased secretion of amylin, and that the resulting hyperamylinemia, which in turn, causes the insulin resistance.

EXAMPLE 15

Production of Transgenic Mice Containing the Agouti cDNA

The clones as described in Examples 11–14 are linearized and microinjected into the pronuclei of fertilized eggs as described in Krimpenfort et al. U.S. Pat. No. 5,175,384; Leder et al. U.S. Pat. No. 5,175,383; Wagner et al. U.S. Pat. No. 5,175,385; Evans et al. U.S. Pat. No. 4,870,009; Berns U.S. Pat. No. 5,174,986, incorporated herein by reference.

Briefly, the DNA fragment used for injection are released from the vector with the appropriate restriction endonucleases and purified by agarose gel electrophoresis and glass-powder purification. The final DNA concentration is adjusted to an appropriate concentration. Fertilized mouse eggs are recover from females. The DNA fragments in a solution at 3–5 µg/ml are injected into the pronucleus of each fertilized egg essentially as described. Hogan, B. L. M. et al., (Cold Spring Harbor Laboratory, Cold Spring Harbor, 1986 *Manipulation of the Mouse Embryo: A Laboratory Animal*). The eggs are transplanted into pseudopregnant female mice for gestation to term. At 3 to 4 week of age, tissue from the tail of the mice is removed. The DNA is analyzed for the presence of the integrated promoter-agouti cDNA-enhancer sequences within the mouse chromosomal DNA, as shown by hybridization to radioactively labeled agouti cDNA probe DNA. Both "Southern blot" and "Northern Blot" hybridizations are performed (Sambrook 1989, ibid). For the hybridization, the chromosomal DNA is digested into fragments using restriction endonuclease which cut the agouti cDNA into known lengths to indicate the authenticity of the added gene. Northern blotting analysis with reveal the size of the mRNA expressed from the transgene. Two transgenic agouti mice are mated and offspring produced to establish a transgenic line.

EXAMPLE 16

Cloning and Characterization the Gene Homologous to Agouti in Humans

Several genes that map close to the agouti locus on mouse chromosome 2 also map to the same relative positions on human chromosome 20. Based on the syntenic relationship between the distal section of mouse chromosome 2 and human chromosome 20, it can be predicted that any human homologue of the agouti gene would also map to human chromosome 20. This is quite significant since a gene associated with mature onset diabetes has also been mapped to human chromosome 20.

Utilizing the full-length mouse agouti cDNA as a probe, the human genome was searched for cross-hybridizing fragments, and a unique-copy cross-hybridizing fragment on human genome blots was identified. This result strongly suggests that there is a unique-copy gene in humans that is homologous to the mouse agouti gene. The cross-hybridizing human fragment is cloned and characterized the structure of the corresponding gene and to map it on the human genome. For this purpose a human genomic library is screened with the mouse cDNA clone. The positive clones are purified, and the specific restriction fragments which cross-hybridize with the mouse cDNA subcloned and sequenced. The gene is mapped using FISH (Fluorescence In Situ Hybridization) map the gene on metaphase human chromosomes utilizing the human genomic clone as a probe using the method as described by Lawrence, J. B., or by both genomic mapping procedures.

EXAMPLE 17

Diagnosis of a Locus Associated Defect

The Agouti gene or analogous genes and mutations in human or other animals may be detected by Southern or Northern blot analyses using radiolabled nucleotide probes. Also, this type of analysis can be accomplished with PCR or RT-PCR technique which have been sesired above. The probes are based on the cDNA sequence of the agouti gene as depicted in FIG. 2 or from substantially homologous sequences or portions thereof.

DNA or RNA samples from test animals are prepared for analysis by techniques known in the art, and a Southern or Northern blot analysis is conducted using the nucleotide probes. The banding pattern of the test sample is compared to a known standard sample pattern.

Differences in the test pattern are indicative of mutations in the gene and are predictive of the development of diabetes, obesity, neoplasms and amylinemia in the test animal.

EXAMPLE 18

Isolation and Characterization of Peptides of the Agouti Gene Product

The agouti gene has the potential to encode a 131 amino acid protein. The agouti protein is secreted since it contains a hydrophobic leader region terming in a consensus signal peptide cleavage site. The 131 amino acid protein (minus its signal peptide) may be the active form of protein or it may require further processing to form a biologically active molecule. Various full length and truncated forms of the protein will be made recombinantly to determine the portions necessary for activity. Comparison of eukaryotic and prokaryoticly expressed proteins will indicate if glycosylation is required for activity. Natural or recombinant protein may be purified by methods known in the art such as affinity chromatography, immunoaffinity chromatography, HPLC and the like.

EXAMPLE 19

Production and Use of Antibodies Specific for the Agouti Gene Products

Recombinant agouti protein is used for the production of antibodies against the agouti protein. The antibody are useful for establishing the location of the agouti gene product within tissues of the animal. Specifically, polyclonal and monoclonal antibodies are prepared utilizing standard procedures, and the titer of the polyclonal antibodies will be determined by standard ELISA. For the RI-agouti transgenics, serum levels of the agouti protein will be established with a standard ELISA analysis. Monoclonal antibodies are produced as previously described above.

Immunohistochemistry is performed on formalin fixed, paraffin embedded tissues using supersensitive biotinylated anti-rabbit antibodies followed by HRP-labeled strepavidin. (Prior to use in histochemistry, the serum will be absorbed with mouse liver powder.) (DAB) (DAB= Diaminobenzidine) is be used as a chromogen color reagent and slides is counterstained with Mayers hematoxylin. Specificity of the staining is controlled by including tissues stained with preimmune rabbit serum treated as above. In addition, anti-agouti serum is passed over an affinity column made of agouti protein coupled to appropriate gel matrix (Reacti-gel, Sepharose, etc.) as well as gels coupled with unrelated proteins. The gel coupled to agouti protein removes all histochemical activity for agouti from the flow through, and the eluted antibody restores the same specific activity.

EXAMPLE 20

Identification of the Receptor/Ligand For the Agouti Gene Product

Since the a locus, like steel, does not act in a cell-autonomous manner, the agouti gene product, like the steel factor, many function as a ligand for receptor on the melanocyte. Interestingly, the extension locus (e) in a chromosome 8 of the mouse acts in a cell-autonomous manner and produces pigmentation phenotypes similar to a. However, dominant e locus mutations cause an all-black phenotype similar to that observed in recessive a locus mutations, and recessive e locus mutations cause an all-yellow phenotype similar to that observed in dominant a locus mutations. Making the assumption that dominant mutations at these two loci are associated with gain of function and recessive mutations are associated with loss of function, a straightforward model (like that for the steel and dominant-white spotting loci) in which the e locus encodes a melanocyte-specific receptor that is directly activated by a ligand produced by the agouti locus is unlikely.

Alternatively, Takeuchi et al. described a model for a potential interaction between the a and e loci based on their experiments with skin explants from A$^y$/a or e/e mice. They proposed that α-melanocyte-stimulating hormone (α-MSH) binds to its receptor on the surface of the melanocyte, triggering a cascade of biochemical events culminating in the elevation of cyclic. AMP levels, which act as a second messenger to produce eumelanin. The e locus hypothetically encodes a protein that modulates the production of cyclic AMP via interaction with adenylate cyclase in the membrane of melanocytes. In this model, the agouti protein may function as a ligand to compete with α-MSH for binding of its receptor, preventing an increase of cyclic AMP in the melanocyte and resulting in the production of phaeomelanin. As discussed above, our finding that the product of the agouti locus may be a small secreted protein is compatible with this model. The agouti gene product shares no sequence homology with α-MSH, and if this model is correct, it is unclear whether the agouti gene product binds directly to α-MSH and inactivate its binding capacity or whether it binds directly to the α-MSH receptor and competitively interfere with the binding of α-MSH.

Using the isolated or recombinant Agouti gene product or fragments and analogs thereof, methods will be devised to determine the receptor for the Agouti gene product and role of receptor in the development of diabetes, obesity, amylinemia and tumors.

EXAMPLE 21

Screening of Drugs For Treatment of Diabetes, obesity, Amylinemia or Tumors

Transgenic animals are prepared as described in Examples 11-15.

To study the effects of potentially therapeutic drugs, 24 transgenic mice are divided into 4 groups. Three groups were fed repelletized Purina 5008 chow and one group of mice are fed the same chow containing the test drug for two weeks. All mice are fed Purina 5008 chow without drug during the third week. Body weight and food consumption are monitored and blood samples are collected before the experiment is initiated (day 0) and after 7 (day 7) and 14 days (day 14) of treatment. Blood samples are collected from tail veins between 0800 and 1000. The 24 mice are bled in the same order each time. Blood samples are analyzed directly for serum amylin.

To test insulin sensitivity after drug treatment, mice are fasted overnight (17 h) from day 14 to day 15. Blood glucose is measured in the morning of day 15 immediately before injections at 0 time. At that time, each mouse receives one i.p injection of 1 g/kg glucose and one i.p. injection of porcine insulin or saline. The two injections are given consecutively on different sides of the abdomen. The 3 control groups are given saline, 0.25 units insulin/kg or 0.5 units insulin/kg, respectively. The drug-treated mice are given 0.25 units insulin/kg. Blood glucose concentrations are then measured at 30, 60 and 120 min after the injections.

Radioimmunoassays kits for insulin are purchased from Diagnostic Products Corporation (San Diego, Calif.). Rat insulin is used as a standard and porcine insulin for injections are obtained at Eli Lilly & Co. (Indianapolis, Ind.). Radioimmunoassay kits for rat amylin are purchased from Peninsula (Belmont, Calif.). The lowest level of detection in the amylin assay is less than 3 pg/assay tube using unextracted plasma (Gill and Yen, 1991 *Life Sciences* 48:703–710). Blood glucose is measured by the glucose oxidase method with a model 300 Alpkem Rapid Flow Analyzer (Clackamaus, Oreg.). Incubating 100 μg drug per ml of blood or plasma are tested to make sure that the drug does not interfere with the assays for blood glucose, plasma insulin, and amylin.

Animals are also monitored for the development of tumors in tissues and size of tumors.

Data are reported as mean ± s.e.m. and analyzed by Student's test or by the two sample t test at each point.

Percent changes of day 0 were calculated individually and reported as mean ± of N=6 or 18 mice. The insulin/amylin ratios are calculated on molar basis.

The above protocol may be varied depending on the drug to be tested. Drug may be given by various routes, for example, intravenously, intraperitonealy, intramuscularly and the like, by bolus injection or continuous infusion, where appropriate. The drug may be given once, twice or the like during the testing interval or may be given daily, as can be determined by those skilled in the art.

What is claimed is:

1. A transgenic mouse expressing an agouti gene product, wherein the germ cells and somatic cells of said mouse comprise a transgene encoding said agouti gene product, wherein said transgene includes in operable linkage a promoter necessary for transcription of said transgene in said mouse, and wherein said agouti gene product is ectopically expressed in said mouse at levels sufficient for said mouse to exhibit insulin-independent diabetes, obesity, hyperamylinemia or tumors in said mouse.

2. The mouse of claim 1, wherein transcription of said transgene is under control of a constitutive promoter.

3. The mouse of claim 2, wherein said constitutive promoter is the human β-actin-promoter.

4. The mouse of claim 2, wherein said promoter is the mouse phosphoglycerate kinase (Pgk-1) promoter.

5. A method of producing the mouse of claim 1 which comprises the steps of:

(a) providing a transgene construct encoding said agouti gene product, wherein said transgene construct includes in operable linkage a promoter necessary for transcription of said transgene in said mouse;

(b) introducing said transgene construct into a mouse embryo;

(c) transplanting said embryo into a pseudopregnant mouse;

(d) allowing said embryo to develop to term;

(e) obtaining a founder mouse carrying said transgene; and (f) breeding said founder mouse with a wild-type mouse to obtain F1 offspring that express the agouti gene product, wherein said F1 offspring exhibit insulin-independent diabetes, obesity, hyperamylinemia or tumors.

6. The method of claim 5, wherein said promoter is a constitutive promoter.

* * * * *